US010045685B2

(12) United States Patent
Bayer et al.

(10) Patent No.: US 10,045,685 B2
(45) Date of Patent: Aug. 14, 2018

(54) ENDOSCOPE

(75) Inventors: Lex Bayer, Palo Alto, CA (US); Fred Rasmussen, Sunnyvale, CA (US)

(73) Assignee: Avantis Medical Systems, Inc., San Jose, CA (US)

( * ) Notice: Subject to any disclaimer, the term of this patent is extended or adjusted under 35 U.S.C. 154(b) by 0 days.

(21) Appl. No.: 13/463,690

(22) Filed: May 3, 2012

(65) Prior Publication Data

US 2013/0116506 A1 May 9, 2013

Related U.S. Application Data

(63) Continuation of application No. 11/626,189, filed on Jan. 23, 2007, now Pat. No. 8,235,887.

(Continued)

(51) Int. Cl.
*A61B 1/00* (2006.01)
*A61B 1/05* (2006.01)
*A61B 1/06* (2006.01)
*A61B 1/31* (2006.01)
*A61B 1/005* (2006.01)

(Continued)

(52) U.S. Cl.
CPC ......... *A61B 1/00181* (2013.01); *A61B 1/005* (2013.01); *A61B 1/0052* (2013.01); *A61B 1/00174* (2013.01); *A61B 1/00177* (2013.01); *A61B 1/00193* (2013.01); *A61B 1/05* (2013.01); *A61B 1/051* (2013.01); *A61B 1/053* (2013.01); *A61B 1/0623* (2013.01); *A61B 1/0676* (2013.01); *A61B 1/273* (2013.01);

(Continued)

(58) Field of Classification Search
CPC .............. A61B 1/0005; A61B 1/00098; A61B 1/00163; A61B 1/00174; A61B 1/00177; A61B 1/00179; A61B 1/00181; A61B 1/00183; A61B 1/00193; A61B 1/05; A61B 1/051; A61B 1/0607; A61B 1/0615; A61B 1/0623; A61B 1/0676; A61B 1/0684
USPC ......... 600/104, 106, 107, 109–113, 160–181
See application file for complete search history.

(56) References Cited

U.S. PATENT DOCUMENTS 1,500,798 A 7/1924 Campodonico
1,509,041 A 9/1924 Hyams
(Continued)

FOREIGN PATENT DOCUMENTS

CN 1628603 A 6/2005
DE 196 26 433 A1 1/1998
(Continued)

OTHER PUBLICATIONS

Advisory Action dated Nov. 2, 2010, for U.S. Appl. No. 11/609,838, filed Dec. 12, 2006, 3 pages.
(Continued)

*Primary Examiner* — Ryan Henderson
(74) *Attorney, Agent, or Firm* — Cooley LLP

(57) ABSTRACT

An endoscope includes an insertion tube having a distal end and an imaging device with a steerable extension. The proximal end of the extension is attached to the distal end of the insertion tube. An endoscope includes an insertion tube having a distal end region and a rear-viewing imaging device at least partially disposed inside the distal end region. An endoscope includes an insertion tube having a distal end cap, an imaging device, and a link that couples the imaging device to the distal end cap of the insertion tube.

22 Claims, 20 Drawing Sheets

Related U.S. Application Data

(60) Provisional application No. 60/761,475, filed on Jan. 23, 2006, provisional application No. 60/802,056, filed on May 19, 2006.

(51) Int. Cl.
   *A61B 1/273* (2006.01)
   *A61B 1/015* (2006.01)
   *A61B 1/018* (2006.01)

(52) U.S. Cl.
   CPC .............. *A61B 1/31* (2013.01); *A61B 1/015* (2013.01); *A61B 1/018* (2013.01)

(56) References Cited

U.S. PATENT DOCUMENTS

| | | |
|---|---|---|
| 3,437,747 A | 4/1969 | Sheldon |
| 3,610,231 A | 10/1971 | Takahashi et al. |
| 3,643,653 A | 2/1972 | Takahashi et al. |
| 3,739,770 A | 6/1973 | Mori |
| 3,889,662 A | 6/1975 | Mitsui |
| 3,897,775 A | 8/1975 | Furihata |
| 3,918,438 A | 11/1975 | Hayamizu et al. |
| 4,066,071 A | 1/1978 | Nagel |
| 4,261,344 A | 4/1981 | Moore et al. |
| 4,279,247 A | 7/1981 | Kinoshita |
| 4,327,711 A | 5/1982 | Takagi |
| 4,351,587 A | 9/1982 | Matsuo et al. |
| 4,398,811 A | 8/1983 | Nishioka et al. |
| 4,494,549 A | 1/1985 | Namba et al. |
| 4,573,450 A | 3/1986 | Arakawa |
| 4,586,491 A | 5/1986 | Carpenter |
| 4,602,281 A | 7/1986 | Nagasaki et al. |
| 4,625,236 A | 11/1986 | Fujimori et al. |
| 4,646,722 A | 3/1987 | Silverstein et al. |
| 4,685,451 A | 8/1987 | Ando |
| 4,699,463 A | 10/1987 | D'Amelio et al. |
| 4,721,097 A | 1/1988 | D'Amelio |
| 4,727,859 A | 3/1988 | Lia |
| 4,741,326 A | 5/1988 | Sidall et al. |
| 4,742,817 A | 5/1988 | Kawashima et al. |
| 4,790,295 A | 12/1988 | Tashiro |
| 4,800,870 A | 1/1989 | Reid, Jr. |
| 4,825,850 A | 5/1989 | Opie et al. |
| 4,836,211 A | 6/1989 | Sekino et al. |
| 4,846,154 A | 7/1989 | MacAnally et al. |
| 4,852,551 A | 8/1989 | Opie et al. |
| 4,853,773 A | 8/1989 | Hibino et al. |
| 4,862,873 A | 9/1989 | Yajima et al. |
| 4,867,138 A | 9/1989 | Kubota et al. |
| 4,869,238 A | 9/1989 | Opie et al. |
| 4,870,488 A | 9/1989 | Ikuno et al. |
| 4,873,572 A | 10/1989 | Miyazaki et al. |
| 4,873,965 A | 10/1989 | Danieli |
| 4,884,133 A | 11/1989 | Kanno et al. |
| 4,899,732 A | 2/1990 | Cohen |
| 4,905,667 A | 3/1990 | Foerster et al. |
| 4,907,395 A | 3/1990 | Opie et al. |
| 4,911,148 A | 3/1990 | Sosnowski et al. |
| 4,911,564 A | 3/1990 | Baker |
| 4,915,626 A | 4/1990 | Lemmey |
| 4,926,258 A | 5/1990 | Sasaki |
| 4,947,827 A | 8/1990 | Opie et al. |
| 4,947,828 A | 8/1990 | Carpenter et al. |
| 4,979,496 A | 12/1990 | Komi |
| 4,991,565 A | 2/1991 | Takahashi et al. |
| 5,010,876 A | 4/1991 | Henley et al. |
| 5,019,040 A | 5/1991 | Itaoka et al. |
| 5,025,778 A | 6/1991 | Silverstein et al. |
| 5,026,377 A | 6/1991 | Burton et al. |
| 5,050,585 A | 9/1991 | Takahashi |
| 5,122,122 A | 6/1992 | Allgood |
| RE34,100 E | 10/1992 | Hartness |
| RE34,110 E | 10/1992 | Opie et al. |
| 5,159,446 A | 10/1992 | Hibino et al. |
| 5,166,787 A | 11/1992 | Irion |
| 5,178,130 A | 1/1993 | Kaiya et al. |
| 5,187,572 A | 2/1993 | Nakamura et al. |
| 5,193,525 A | 3/1993 | Silverstein et al. |
| 5,196,928 A | 3/1993 | Karasawa et al. |
| 5,253,638 A | 10/1993 | Tamburrino et al. |
| 5,260,780 A | 11/1993 | Staudt, III |
| 5,271,381 A | 12/1993 | Ailinger et al. |
| 5,305,121 A | 4/1994 | Moll |
| 5,318,031 A | 6/1994 | Mountford et al. |
| 5,329,887 A | 7/1994 | Ailinger et al. |
| 5,337,734 A | 8/1994 | Saab |
| 5,381,784 A | 1/1995 | Adair |
| 5,398,685 A | 3/1995 | Wilk et al. |
| 5,406,938 A | 4/1995 | Mersch et al. |
| 5,434,669 A | 7/1995 | Tabata et al. |
| 5,443,781 A | 8/1995 | Saab |
| 5,447,148 A | 9/1995 | Oneda et al. |
| 5,483,951 A | 1/1996 | Frassica et al. |
| 5,494,483 A | 2/1996 | Adair |
| 5,518,501 A | 5/1996 | Oneda et al. |
| 5,520,607 A | 5/1996 | Frassica et al. |
| 5,530,238 A | 6/1996 | Meulenbrugge et al. |
| 5,533,496 A | 7/1996 | De Faira-Correa et al. |
| 5,536,236 A | 7/1996 | Yabe et al. |
| 5,547,455 A * | 8/1996 | McKenna ............ A61B 1/0005 348/65 |
| 5,556,367 A | 9/1996 | Yabe et al. |
| 5,613,936 A | 3/1997 | Czarnek et al. |
| 5,614,943 A | 3/1997 | Nakamura et al. |
| 5,626,553 A | 5/1997 | Frassica et al. |
| 5,634,466 A | 6/1997 | Gruner |
| 5,653,677 A | 8/1997 | Okada et al. |
| 5,667,476 A | 9/1997 | Frassica et al. |
| 5,679,216 A | 10/1997 | Takayama et al. |
| 5,681,260 A | 10/1997 | Ueda et al. |
| 5,682,199 A | 10/1997 | Lankford |
| 5,685,822 A | 11/1997 | Harhen |
| 5,692,729 A | 12/1997 | Harhen |
| 5,696,850 A | 12/1997 | Parulski et al. |
| 5,702,348 A | 12/1997 | Harhen |
| 5,706,128 A | 1/1998 | Greenberg |
| 5,711,299 A | 1/1998 | Manwaring et al. |
| 5,722,933 A | 3/1998 | Yabe et al. |
| 5,752,912 A | 5/1998 | Takahashi et al. |
| 5,762,603 A | 6/1998 | Thompson |
| 5,782,751 A | 7/1998 | Matsuno |
| 5,800,341 A | 9/1998 | Mckenna et al. |
| 5,817,061 A | 10/1998 | Goodwin et al. |
| 5,827,177 A | 10/1998 | Oneda et al. |
| 5,833,603 A | 11/1998 | Kovacs et al. |
| 5,843,103 A | 12/1998 | Wulfman |
| 5,843,460 A | 12/1998 | Labigne et al. |
| 5,854,859 A | 12/1998 | Sobol |
| 5,860,914 A | 1/1999 | Chiba et al. |
| 5,876,329 A | 3/1999 | Harhen |
| 5,916,147 A | 6/1999 | Boury |
| 5,924,977 A | 7/1999 | Yabe et al. |
| 5,938,587 A | 8/1999 | Taylor et al. |
| 5,947,905 A | 9/1999 | Hadjicostis et al. |
| 5,982,932 A | 11/1999 | Prokoski |
| 5,989,182 A | 11/1999 | Hori et al. |
| 5,989,224 A | 11/1999 | Exline et al. |
| 6,017,358 A | 1/2000 | Yoon |
| 6,026,323 A | 2/2000 | Skladnev et al. |
| 6,066,090 A | 5/2000 | Yoon |
| 6,071,233 A | 6/2000 | Ishikawa et al. |
| 6,099,464 A | 8/2000 | Shimizu et al. |
| 6,099,466 A | 8/2000 | Sano et al. |
| 6,099,485 A | 8/2000 | Patterson |
| 6,106,463 A | 8/2000 | Wilk |
| 6,154,315 A | 11/2000 | Street |
| 6,174,280 B1 | 1/2001 | Oneda et al. |
| 6,190,330 B1 | 2/2001 | Harhen |
| 6,203,493 B1 | 3/2001 | Ben-Haim |
| 6,214,028 B1 | 4/2001 | Yoon et al. |
| 6,216,226 B1 | 4/2001 | Agha et al. |
| 6,261,226 B1 | 7/2001 | McKenna et al. |
| 6,261,307 B1 | 7/2001 | Yoon et al. |

(56) References Cited

U.S. PATENT DOCUMENTS

| | | |
|---|---|---|
| 6,277,064 B1 | 8/2001 | Yoon |
| 6,296,608 B1 | 10/2001 | Daniels et al. |
| 6,301,047 B1 | 10/2001 | Hoshino et al. |
| 6,350,231 B1 | 2/2002 | Ailinger et al. |
| 6,364,829 B1 | 4/2002 | Fulghum |
| 6,369,855 B1 | 4/2002 | Chauvel et al. |
| 6,375,653 B1 | 4/2002 | Desai |
| 6,387,043 B1 | 5/2002 | Yoon |
| 6,433,492 B1 | 8/2002 | Buonavita |
| 6,450,950 B2 | 9/2002 | Irion |
| 6,454,702 B1 | 9/2002 | Smith |
| 6,456,684 B1 | 9/2002 | Mun et al. |
| 6,461,294 B1 | 10/2002 | Oneda et al. |
| 6,464,633 B1 | 10/2002 | Hosoda et al. |
| 6,482,149 B1 | 11/2002 | Torii |
| 6,503,195 B1 | 1/2003 | Keller et al. |
| 6,527,704 B1 | 3/2003 | Chang et al. |
| 6,547,724 B1 | 4/2003 | Soble et al. |
| 6,554,767 B2 | 4/2003 | Tanaka |
| 6,564,088 B1 | 5/2003 | Soller et al. |
| 6,638,214 B2 | 10/2003 | Akiba |
| 6,640,017 B1 | 10/2003 | Tsai et al. |
| 6,648,816 B2 | 11/2003 | Irion et al. |
| 6,683,716 B1 | 1/2004 | Costales |
| 6,687,010 B1 | 2/2004 | Horii et al. |
| 6,697,536 B1 | 2/2004 | Yamada |
| 6,699,180 B2 | 3/2004 | Kobayashi |
| 6,736,773 B2 | 5/2004 | Wendlandt et al. |
| 6,748,975 B2 | 6/2004 | Hartshorne et al. |
| 6,796,939 B1 | 9/2004 | Hirata et al. |
| 6,833,871 B1 | 12/2004 | Merrill et al. |
| 6,845,190 B1 | 1/2005 | Smithwick et al. |
| 6,891,977 B2 | 5/2005 | Gallagher |
| 6,916,286 B2 | 7/2005 | Kazakevich |
| 6,928,314 B1 | 8/2005 | Johnson et al. |
| 6,929,636 B1 | 8/2005 | von Alten |
| 6,947,784 B2 | 9/2005 | Zalis |
| 6,951,536 B2 | 10/2005 | Yokoi et al. |
| 6,965,702 B2 | 11/2005 | Gallagher |
| 6,966,906 B2 | 11/2005 | Brown |
| 6,974,240 B2 | 12/2005 | Takahashi |
| 6,974,411 B2 | 12/2005 | Belson |
| 6,992,694 B2 | 1/2006 | Abe |
| 6,997,871 B2 | 2/2006 | Sonnenschein et al. |
| 7,004,900 B2 | 2/2006 | Wendlandt et al. |
| 7,017,345 B2 | 3/2006 | Von Behrens et al. |
| 7,029,435 B2 | 4/2006 | Nakao |
| 7,041,050 B1 | 5/2006 | Ronald |
| 7,095,548 B1 | 8/2006 | Cho et al. |
| 7,103,228 B2 | 9/2006 | Kraft et al. |
| 7,116,352 B2 | 10/2006 | Yaron |
| 7,173,656 B1 | 2/2007 | Dunton et al. |
| 7,228,004 B2 | 6/2007 | Gallagher et al. |
| 7,258,663 B2 | 8/2007 | Doguchi et al. |
| 7,280,141 B1 | 10/2007 | Frank et al. |
| 7,317,458 B2 | 1/2008 | Wada |
| 7,322,934 B2 | 1/2008 | Miyake et al. |
| 7,341,555 B2 | 3/2008 | Ootawara et al. |
| 7,362,911 B1 | 4/2008 | Frank |
| 7,389,892 B2 | 6/2008 | Park |
| 7,405,877 B1 | 7/2008 | Schechterman |
| 7,435,218 B2 | 10/2008 | Krattiger et al. |
| 7,436,562 B2 | 10/2008 | Nagasawa et al. |
| 7,507,200 B2 | 3/2009 | Okada |
| 7,551,196 B2 | 6/2009 | Ono et al. |
| 7,556,599 B2 | 7/2009 | Rovegno |
| 7,561,190 B2 | 7/2009 | Deng et al. |
| 7,621,869 B2 | 11/2009 | Ratnakar |
| 7,646,520 B2 | 1/2010 | Funaki et al. |
| 7,662,089 B2 | 2/2010 | Okada et al. |
| 7,678,043 B2 | 3/2010 | Gilad |
| 7,683,926 B2 | 3/2010 | Schechterman et al. |
| 7,749,156 B2 | 7/2010 | Ouchi |
| 7,825,964 B2 | 11/2010 | Hoshino et al. |
| 7,846,215 B2 | 12/2010 | Weber et al. |
| 7,864,215 B2 | 1/2011 | Carlsson et al. |
| 7,910,295 B2 | 3/2011 | Hoon et al. |
| 7,922,655 B2 | 4/2011 | Yasushi et al. |
| 7,927,272 B2 | 4/2011 | Bayer et al. |
| 8,009,167 B2 | 8/2011 | Dekel et al. |
| 8,064,666 B2 | 11/2011 | Bayer |
| 8,070,743 B2 | 12/2011 | Kagan et al. |
| 8,165,358 B2 | 4/2012 | Sirohey et al. |
| 8,182,422 B2 | 5/2012 | Bayer et al. |
| 8,197,399 B2 | 6/2012 | Bayer et al. |
| 8,235,887 B2 | 8/2012 | Bayer et al. |
| 8,287,446 B2 | 10/2012 | Bayer |
| 8,289,381 B2 | 10/2012 | Bayer et al. |
| 8,310,530 B2 | 11/2012 | Bayer et al. |
| 8,419,630 B2 | 4/2013 | Kase et al. |
| 8,587,645 B2 | 11/2013 | Bayer et al. |
| 8,797,392 B2 | 8/2014 | Bayer et al. |
| 8,872,906 B2 | 10/2014 | Bayer et al. |
| 8,926,502 B2 | 1/2015 | Levy et al. |
| 9,044,185 B2 | 6/2015 | Bayer |
| 9,613,418 B2 | 4/2017 | Bayer |
| 2001/0007468 A1 | 7/2001 | Sugimoto et al. |
| 2001/0031912 A1 | 10/2001 | Adler |
| 2001/0037052 A1 | 11/2001 | Higuchi et al. |
| 2001/0051766 A1 | 12/2001 | Gazdinski |
| 2001/0056238 A1 | 12/2001 | Tsujita |
| 2002/0022769 A1 | 2/2002 | Smith et al. |
| 2002/0026188 A1 | 2/2002 | Balbierz et al. |
| 2002/0039400 A1 | 4/2002 | Kaufman et al. |
| 2002/0089584 A1 | 7/2002 | Abe |
| 2002/0095168 A1 | 7/2002 | Griego et al. |
| 2002/0099267 A1 | 7/2002 | Wendlandt et al. |
| 2002/0101546 A1 | 8/2002 | Sharp et al. |
| 2002/0103420 A1 | 8/2002 | Coleman et al. |
| 2002/0110282 A1 | 8/2002 | Kraft et al. |
| 2002/0115908 A1 | 8/2002 | Farkas et al. |
| 2002/0156347 A1 | 10/2002 | Kim et al. |
| 2002/0165444 A1 | 11/2002 | Whitman |
| 2002/0193662 A1 | 12/2002 | Belson |
| 2003/0001951 A1 | 1/2003 | Tsujita et al. |
| 2003/0004399 A1 | 1/2003 | Belson |
| 2003/0011768 A1 | 1/2003 | Jung et al. |
| 2003/0032863 A1 | 2/2003 | Kazakevich et al. |
| 2003/0040668 A1 | 2/2003 | Kaneko et al. |
| 2003/0045778 A1 | 3/2003 | Ohline et al. |
| 2003/0065250 A1 | 4/2003 | Chiel et al. |
| 2003/0088152 A1 | 5/2003 | Takada |
| 2003/0093031 A1 | 5/2003 | Long et al. |
| 2003/0093088 A1 | 5/2003 | Long et al. |
| 2003/0103199 A1 | 6/2003 | Jung et al. |
| 2003/0105386 A1 | 6/2003 | Voloshin et al. |
| 2003/0120130 A1 | 6/2003 | Glukhovsky |
| 2003/0125630 A1 | 7/2003 | Furnish |
| 2003/0125788 A1 | 7/2003 | Long |
| 2003/0128892 A1 | 7/2003 | Avinash |
| 2003/0130711 A1 | 7/2003 | Pearson et al. |
| 2003/0153866 A1 | 8/2003 | Long et al. |
| 2003/0161545 A1 | 8/2003 | Gallagher |
| 2003/0161554 A1 | 8/2003 | Patridge et al. |
| 2003/0167007 A1 | 9/2003 | Belson |
| 2003/0171650 A1 | 9/2003 | Tartaglia et al. |
| 2003/0176767 A1 | 9/2003 | Long et al. |
| 2003/0179302 A1 | 9/2003 | Harada et al. |
| 2003/0187326 A1 | 10/2003 | Chang |
| 2003/0195545 A1 | 10/2003 | Hermann et al. |
| 2003/0197781 A1 | 10/2003 | Sugimoto et al. |
| 2003/0197793 A1 | 10/2003 | Mitsunaga et al. |
| 2003/0215788 A1 | 11/2003 | Long |
| 2003/0225433 A1 | 12/2003 | Nakao |
| 2003/0233115 A1 | 12/2003 | Eversull et al. |
| 2004/0015049 A1 | 1/2004 | Zaar |
| 2004/0023397 A1 | 2/2004 | Vig et al. |
| 2004/0034278 A1 | 2/2004 | Adams |
| 2004/0049096 A1 | 3/2004 | Adams |
| 2004/0059191 A1 | 3/2004 | Krupa et al. |
| 2004/0080613 A1 | 4/2004 | Moriyama |
| 2004/0085443 A1 | 5/2004 | Kallioniemi et al. |
| 2004/0097790 A1 | 5/2004 | Farkas et al. |
| 2004/0109164 A1 | 6/2004 | Horii et al. |

(56) References Cited

U.S. PATENT DOCUMENTS

| | | |
|---|---|---|
| 2004/0109319 A1 | 6/2004 | Takahashi |
| 2004/0111019 A1 | 6/2004 | Long |
| 2004/0122291 A1 | 6/2004 | Takahashi |
| 2004/0141054 A1 | 7/2004 | Mochida et al. |
| 2004/0158124 A1 | 8/2004 | Okada |
| 2004/0207618 A1 | 10/2004 | Williams et al. |
| 2004/0228544 A1 | 11/2004 | Endo et al. |
| 2004/0242963 A1 | 12/2004 | Matsumoto et al. |
| 2004/0242987 A1 | 12/2004 | Liew et al. |
| 2004/0249247 A1 | 12/2004 | Iddan |
| 2005/0004474 A1 | 1/2005 | Iddan |
| 2005/0010084 A1 | 1/2005 | Tsai |
| 2005/0014996 A1 | 1/2005 | Konomura et al. |
| 2005/0020918 A1 | 1/2005 | Wilk et al. |
| 2005/0020926 A1 | 1/2005 | Wiklof et al. |
| 2005/0038317 A1 | 2/2005 | Ratnakar |
| 2005/0038319 A1 | 2/2005 | Goldwasser et al. |
| 2005/0068431 A1 | 3/2005 | Mori |
| 2005/0085693 A1 | 4/2005 | Belson et al. |
| 2005/0085790 A1 | 4/2005 | Guest et al. |
| 2005/0096502 A1 | 5/2005 | Khalili |
| 2005/0154278 A1 | 7/2005 | Cabiri et al. |
| 2005/0165272 A1 | 7/2005 | Okada et al. |
| 2005/0165279 A1 | 7/2005 | Adler et al. |
| 2005/0177024 A1 | 8/2005 | Mackin |
| 2005/0203420 A1 | 9/2005 | Kleen et al. |
| 2005/0215911 A1 | 9/2005 | Alfano et al. |
| 2005/0222500 A1 | 10/2005 | Itoi |
| 2005/0228224 A1 | 10/2005 | Okada et al. |
| 2005/0234297 A1 | 10/2005 | Devierre et al. |
| 2005/0267361 A1 | 12/2005 | Younker et al. |
| 2005/0272975 A1 | 12/2005 | McWeeney et al. |
| 2005/0272977 A1 | 12/2005 | Saadat et al. |
| 2006/0022234 A1 | 2/2006 | Adair et al. |
| 2006/0044267 A1 | 3/2006 | Xie et al. |
| 2006/0052709 A1 | 3/2006 | DeBaryshe et al. |
| 2006/0058584 A1 | 3/2006 | Hirata |
| 2006/0061680 A1 | 3/2006 | Madhavan et al. |
| 2006/0106286 A1 | 5/2006 | Wendlandt et al. |
| 2006/0114986 A1 | 6/2006 | Knapp et al. |
| 2006/0144986 A1 | 7/2006 | Tsai |
| 2006/0149127 A1 | 7/2006 | Seddiqui et al. |
| 2006/0149129 A1 | 7/2006 | Watts et al. |
| 2006/0183975 A1 | 8/2006 | Saadat et al. |
| 2006/0184037 A1 | 8/2006 | Ince et al. |
| 2006/0217594 A1 | 9/2006 | Ferguson |
| 2006/0238614 A1 | 10/2006 | Konno |
| 2006/0250503 A1 | 11/2006 | Crutchfield, Jr. et al. |
| 2006/0252994 A1* | 11/2006 | Ratnakar ............... 600/173 |
| 2006/0279632 A1 | 12/2006 | Anderson |
| 2006/0280360 A1 | 12/2006 | Holub |
| 2006/0285766 A1 | 12/2006 | Ali |
| 2006/0293562 A1 | 12/2006 | Uchimura et al. |
| 2007/0015967 A1 | 1/2007 | Boulais et al. |
| 2007/0015989 A1 | 1/2007 | Desai et al. |
| 2007/0066868 A1 | 3/2007 | Shikii |
| 2007/0083081 A1 | 4/2007 | Schlagenhauf et al. |
| 2007/0097206 A1 | 5/2007 | Houvener et al. |
| 2007/0103460 A1 | 5/2007 | Zhang et al. |
| 2007/0118017 A1 | 5/2007 | Honda |
| 2007/0142711 A1 | 6/2007 | Bayer et al. |
| 2007/0173686 A1 | 7/2007 | Lin et al. |
| 2007/0177008 A1 | 8/2007 | Bayer et al. |
| 2007/0177009 A1 | 8/2007 | Bayer et al. |
| 2007/0183685 A1 | 8/2007 | Wada et al. |
| 2007/0185384 A1 | 8/2007 | Bayer et al. |
| 2007/0203396 A1 | 8/2007 | McCutcheon et al. |
| 2007/0225552 A1 | 9/2007 | Segawa et al. |
| 2007/0225554 A1 | 9/2007 | Maseda et al. |
| 2007/0225734 A1 | 9/2007 | Bell et al. |
| 2007/0238927 A1 | 10/2007 | Ueno et al. |
| 2007/0244354 A1 | 10/2007 | Bayer |
| 2007/0270642 A1 | 11/2007 | Bayer et al. |
| 2007/0279486 A1 | 12/2007 | Bayer et al. |
| 2007/0280669 A1 | 12/2007 | Karim |
| 2007/0293720 A1 | 12/2007 | Bayer |
| 2008/0015409 A1 | 1/2008 | Barlow et al. |
| 2008/0021269 A1 | 1/2008 | Tinkham et al. |
| 2008/0021274 A1 | 1/2008 | Bayer et al. |
| 2008/0033450 A1 | 2/2008 | Bayer et al. |
| 2008/0039693 A1 | 2/2008 | Karasawa |
| 2008/0045789 A1 | 2/2008 | Sawachi |
| 2008/0064931 A1 | 3/2008 | Schena et al. |
| 2008/0065110 A1 | 3/2008 | Duval et al. |
| 2008/0071291 A1 | 3/2008 | Duval et al. |
| 2008/0079827 A1 | 4/2008 | Hoshino et al. |
| 2008/0084478 A1 | 4/2008 | Gilad et al. |
| 2008/0097292 A1 | 4/2008 | Cabiri et al. |
| 2008/0114288 A1 | 5/2008 | Whayne et al. |
| 2008/0130108 A1 | 6/2008 | Bayer et al. |
| 2008/0154288 A1 | 6/2008 | Belson |
| 2008/0199829 A1 | 8/2008 | Paley et al. |
| 2008/0200763 A1 | 8/2008 | Ueno |
| 2008/0253686 A1 | 10/2008 | Bayer |
| 2008/0275298 A1 | 11/2008 | Ratnakar |
| 2009/0015842 A1 | 1/2009 | Leitgeb et al. |
| 2009/0023998 A1 | 1/2009 | Ratnakar |
| 2009/0028407 A1 | 1/2009 | Seibel et al. |
| 2009/0036739 A1 | 2/2009 | Hadani |
| 2009/0049627 A1 | 2/2009 | Kritzler |
| 2009/0082629 A1 | 3/2009 | Dotan et al. |
| 2009/0105538 A1 | 4/2009 | Van Dam et al. |
| 2009/0137867 A1 | 5/2009 | Goto |
| 2009/0208071 A1 | 8/2009 | Nishimura et al. |
| 2009/0213211 A1 | 8/2009 | Bayer et al. |
| 2009/0231419 A1 | 9/2009 | Bayer |
| 2010/0217076 A1 | 8/2010 | Ratnakar |
| 2011/0160535 A1 | 6/2011 | Bayer et al. |
| 2011/0213206 A1 | 9/2011 | Boutillette et al. |
| 2011/0263938 A1 | 10/2011 | Levy |
| 2012/0024026 A1 | 2/2012 | Varadachari |
| 2012/0033062 A1 | 2/2012 | Bayer |
| 2012/0053407 A1 | 3/2012 | Levy |
| 2012/0065468 A1 | 3/2012 | Levy et al. |
| 2012/0209071 A1 | 8/2012 | Bayer et al. |
| 2012/0224026 A1 | 9/2012 | Bayer et al. |
| 2012/0229615 A1 | 9/2012 | Kirma et al. |
| 2012/0232340 A1 | 9/2012 | Levy et al. |
| 2012/0232343 A1 | 9/2012 | Levy et al. |
| 2012/0232345 A1 | 9/2012 | Levy et al. |
| 2012/0300999 A1 | 11/2012 | Bayer |
| 2013/0012778 A1 | 1/2013 | Bayer et al. |
| 2013/0109916 A1 | 5/2013 | Levy |
| 2013/0150671 A1 | 6/2013 | Levy et al. |
| 2013/0172670 A1 | 7/2013 | Levy et al. |
| 2013/0172676 A1 | 7/2013 | Levy et al. |
| 2013/0197304 A1 | 8/2013 | Bayer et al. |
| 2013/0274551 A1 | 10/2013 | Kirma et al. |
| 2013/0296649 A1 | 11/2013 | Kirma et al. |
| 2014/0018624 A1 | 1/2014 | Bayer et al. |
| 2014/0046136 A1 | 2/2014 | Bayer et al. |
| 2014/0213850 A1 | 7/2014 | Levy et al. |
| 2014/0296643 A1 | 10/2014 | Levy et al. |
| 2014/0296866 A1 | 10/2014 | Salman et al. |
| 2014/0336459 A1 | 11/2014 | Bayer et al. |
| 2014/0343358 A1 | 11/2014 | Hameed et al. |
| 2015/0201827 A1 | 7/2015 | Sidar |
| 2015/0223676 A1 | 8/2015 | Bayer et al. |
| 2016/0086331 A1 | 3/2016 | Bayer |

FOREIGN PATENT DOCUMENTS

| | | |
|---|---|---|
| DE | 20 2006 017 173 U1 | 3/2007 |
| EP | 0 586 162 A1 | 3/1994 |
| EP | 1 570 778 A1 | 9/2005 |
| EP | 1 769 720 A1 | 4/2007 |
| FR | 711 949 | 9/1931 |
| JP | 49-130235 A | 12/1974 |
| JP | 56-9712 A | 1/1981 |
| JP | 56-56486 A | 5/1981 |
| JP | 57-170707 A | 10/1982 |
| JP | 60-83636 A | 5/1985 |

(56) References Cited

FOREIGN PATENT DOCUMENTS

| | | | |
|---|---|---|---|
| JP | 60-111217 A | 6/1985 |
| JP | 62-094312 U1 | 6/1987 |
| JP | 63-309912 A | 12/1988 |
| JP | 1-267514 A | 10/1989 |
| JP | 1-172847 U | 12/1989 |
| JP | 2-295530 A | 12/1990 |
| JP | 3-159629 A | 7/1991 |
| JP | 4-500768 A | 2/1992 |
| JP | 4-341232 A | 11/1992 |
| JP | 5-285091 A | 11/1993 |
| JP | 5-307144 A | 11/1993 |
| JP | 5-341210 A | 12/1993 |
| JP | 6-9228 B2 | 2/1994 |
| JP | 60-76714 A | 3/1994 |
| JP | 6-130308 A | 5/1994 |
| JP | 6-169880 A | 6/1994 |
| JP | 7-352 A | 1/1995 |
| JP | 7-354 A | 1/1995 |
| JP | 7-021001 U | 4/1995 |
| JP | 7-275197 A | 10/1995 |
| JP | 8-24208 A | 1/1996 |
| JP | 8-206061 A | 8/1996 |
| JP | 9-56662 A | 3/1997 |
| JP | 7-136108 A | 5/1998 |
| JP | 11-76150 A | 3/1999 |
| JP | 11-253401 A | 9/1999 |
| JP | 11-332821 A | 12/1999 |
| JP | 2003-135388 A | 5/2003 |
| JP | 2003-220023 A | 8/2003 |
| JP | 2004-065971 A | 3/2004 |
| JP | 2004-202252 A | 7/2004 |
| JP | 2004-525717 A | 8/2004 |
| JP | 2004-537362 A | 12/2004 |
| JP | 2007-143580 A | 6/2007 |
| WO | WO-93/15648 A1 | 8/1993 |
| WO | WO-99/17542 A1 | 4/1999 |
| WO | WO-99/30506 A1 | 6/1999 |
| WO | WO-02/085194 A1 | 10/2002 |
| WO | WO-02/094105 A2 | 11/2002 |
| WO | WO-02/094105 A3 | 11/2002 |
| WO | WO-03/013349 A2 | 2/2003 |
| WO | WO-03/013349 A3 | 2/2003 |
| WO | 2005/110186 A2 | 11/2005 |
| WO | WO-2006/073676 A1 | 7/2006 |
| WO | WO-2006/073725 A1 | 7/2006 |
| WO | WO-2006/087981 A1 | 8/2006 |
| WO | WO-2006/110275 A2 | 10/2006 |
| WO | WO-2006/110275 A3 | 10/2006 |
| WO | WO-2007/015241 A2 | 2/2007 |
| WO | WO-2007/015241 A3 | 2/2007 |
| WO | WO-2007/070644 A2 | 6/2007 |
| WO | WO-2007/070644 A3 | 6/2007 |
| WO | WO-2007/087421 A2 | 8/2007 |
| WO | WO-2007/087421 A3 | 8/2007 |
| WO | WO-2007/092533 A2 | 8/2007 |
| WO | WO-2007/092533 A3 | 8/2007 |
| WO | WO-2007/092636 A2 | 8/2007 |
| WO | WO-2007/092636 A3 | 8/2007 |
| WO | WO-2007/136859 A2 | 11/2007 |
| WO | WO-2007/136859 A3 | 11/2007 |
| WO | WO-2007/136879 A2 | 11/2007 |
| WO | WO-2007/136879 A3 | 11/2007 |
| WO | 2007/136879 B1 | 5/2008 |
| WO | WO-2009/014895 A1 | 1/2009 |
| WO | WO-2009/015396 A2 | 1/2009 |
| WO | WO-2009/015396 A3 | 1/2009 |
| WO | 2009/049324 A1 | 4/2009 |
| WO | WO-2009/049322 A2 | 4/2009 |
| WO | WO-2009/049322 A3 | 4/2009 |
| WO | WO-2009/062179 A1 | 5/2009 |
| WO | WO-2012/038958 A2 | 3/2012 |
| WO | WO-2012/038958 A3 | 3/2012 |
| WO | WO-2014/186775 A1 | 11/2014 |

OTHER PUBLICATIONS

Advisory Action dated May 23, 2011, for U.S. Appl. No. 11/751,605, filed May 21, 2007, 3 pages.
Amendment in Response to Non-Final Office Action filed on Jun. 25, 2010, for U.S. Appl. No. 11/609,838, filed Dec. 12, 2006, 14 pages.
Amendment in Response to Non-Final Office Action filed on Jun. 29, 2009, for U.S. Appl. No. 11/215,660, filed Aug. 29, 2005, 9 pages.
Amendment in Response to Final Office Action filed on Mar. 8, 2010, for U.S. Appl. No. 11/215,660, filed Aug. 29, 2005, 11 pages.
Amendment in Response to Non-Final Office Action filed on Aug. 30, 2010, for U.S. Appl. No. 11/215,660, filed Aug. 29, 2005, 17 pages.
Amendment in Response to Final Office Action filed on Oct. 22, 2010, for U.S. Appl. No. 11/609,838, filed Dec. 12, 2006, 15 pages.
Amendment in Response to Non-Final Office Action filed on Oct. 22, 2010, for U.S. Appl. No. 11/834,540, filed Aug. 6, 2007, 13 pages.
Amendment in Response to Non-Final Office Action filed on Feb. 9, 2011, for U.S. Appl. No. 11/828,835, filed Jul. 26, 2007, 10 pages.
Amendment in Response to Non-Final Office Action filed on Feb. 25, 2011, for U.S. Appl. No. 11/751,605, filed May 21, 2007, 15 pages.
Amendment in Response to Final Office Action filed on Feb. 28, 2011, for U.S. Appl. No. 11/215,660, filed Aug. 29, 2005, 11 pages.
Amendment in Response to Non-Final Office Action filed on Apr. 12, 2011, for U.S. Appl. No. 11/626,189, filed Jan. 23, 2007, 18 pages.
Amendment in Response to Non-Final Office Action filed on May 17, 2011, for U.S. Appl. No. 11/609,838, filed Dec. 12, 2006, 18 pages.
Amendment in Response to Final Office Action filed on May 17, 2011, for U.S. Appl. No. 11/751,605, filed May 21, 2007, 10 pages.
Amendment in Response to Final Office Action filed on May 24, 2011, for U.S. Appl. No. 11/828,835, filed Jul. 26, 2007, 13 pages.
Amendment in Response to Non-Final Office Action filed on May 24, 2011, for U.S. Appl. No. 11/736,438, filed Apr. 17, 2007, 11 pages.
Amendment in Response to Non-Final Office Action filed on Jun. 6, 2011, for U.S. Appl. No. 12/101,050, filed Apr. 10, 2008, 17 pages.
Amendment in Response to Final Office Action filed on Jun. 7, 2011, for U.S. Appl. No. 11/751,605, filed May 21, 2007, 11 pages.
Amendment in Response to Final Office Action filed on Dec. 7, 2011, for U.S. Appl. No. 11/736,438, filed Apr. 17, 2007, 10 pages.
Amendment in Response to Non-Final Office Action filed on Dec. 16, 2011, for U.S. Appl. No. 11/938,256, filed Nov. 10, 2007, 10 pages.
Amendment in Response to Non-Final Office Action filed on Jan. 9, 2012, for U.S. Appl. No. 11/751,596, filed May 21, 2007, 9 pages.
Amendment in Response to Non-Final Office Action filed on Feb. 15, 2012, for U.S. Appl. No. 11/626,189, filed Jan. 23, 2007, 13 pages.
Amendment in Response to Non-Final Office Action filed on Feb. 17, 2012, for U.S. Appl. No. 11/751,597, filed May 21, 2007, 18 pages.
Amendment in Response to Non-Final Office Action filed on Mar. 23, 2012, for U.S. Appl. No. 11/672,020, filed Feb. 6, 2007, 12 pages.
European Communication dated Jan. 22, 2009, for European Application No. 07777255.6, filed on May 21, 2007, 2 pages.
European Office Action dated May 5, 2009, for European Patent Application No. 07763368.3, filed on Feb. 6, 2007, 3 pages.
European Office Action dated Feb. 5, 2010, for European Patent Application No. 06845440.4, filed on Dec. 13, 2006, 4 pages.
European Office Action dated Apr. 1, 2010, for European Patent Application No. 07717235.1, filed on Feb. 9, 2007, 2 pages.
European Office Action dated Nov. 8, 2010, for European Patent Application No. 05854262.2, filed on Dec. 8, 2005, 5 pages.
European Office Action dated Jun. 14, 2011, for European Patent Application No. 07795177.0, filed on May 21, 2007, 6 pages.

(56) References Cited

OTHER PUBLICATIONS

European Office Action dated May 21, 2012, for European Patent Application No. 06845440.4, filed on Jul. 10, 2008, 6 pages.
European Office Action dated May 21, 2012, for European Patent Application No. 07717024.9, filed on Aug. 21, 2008, 5 pages.
European Office Action dated May 21, 2012, for European Patent Application No. 07717235.1, filed on Sep. 5, 2008, 5 pages.
Extended European Search Report dated Apr. 26, 2012, for European Patent Application No. 12153946.4, filed Feb. 3, 2012, 6 pages.
Extended European Search Report dated Oct. 5, 2012, for European Patent Application No. 12162806.9, filed Apr. 2, 2012, 5 pages.
Final Office Action dated Oct. 8, 2009, for U.S. Appl. No. 11/215,660, filed Aug. 29, 2005, 12 pages.
Final Office Action dated Aug. 23, 2010, for U.S. Appl. No. 11/609,838, filed Dec. 12, 2006, 20 pages.
Final Office Action dated Nov. 1, 2010, for U.S. Appl. No. 11/215,660, filed Aug. 29, 2005, 12 pages.
Final Office Action dated Mar. 22, 2011, for U.S. Appl. No. 11/828,835, filed Jul. 26, 2007, 11 pages.
Final Office Action dated Apr. 29, 2011, for U.S. Appl. No. 11/751,605, filed May 21, 2007, 9 pages.
Final Office Action dated Aug. 3, 2011, for U.S. Appl. No. 11/736,438, filed Apr. 17, 2007, 11 pages.
Final Office Action dated Apr. 23, 2012, for U.S. Appl. No. 11/938,256, filed Nov. 10, 2007, 13 pages.
Final Office Action dated Apr. 25, 2012, for U.S. Appl. No. 12/251,406, filed Oct. 14, 2008, 10 pages.
Final Office Action dated Aug. 1, 2012, for U.S. Appl. No. 11/673,470 filed Nov. 10, 2007, 33 pages.
International Search Report dated May 18, 2006, for PCT Patent Application No. PCT/US2005/045499, filed on Dec. 8, 2005, 4 pages.
International Search Report dated May 19, 2006, for PCT Patent Application No. PCT/US2005/044624, filed on Dec. 8, 2005, 4 pages.
International Search Report dated Jun. 20, 2007, for PCT Patent Application No. PCT/US2006/047748, filed on Dec. 13, 2006, 3 pages.
International Search Report dated Sep. 28, 2007, for PCT Patent Application No. PCT/US2007/002096 filed on Jan. 23, 2007, 4 pages.
International Search Report dated Oct. 25, 2007, for PCT Patent Application No. PCT/US2007/003322, filed on Feb. 6, 2007, 5 pages.
International Search Report dated Oct. 26, 2007, for PCT Patent Application No. PCT/US2007/003631, filed on Feb. 9, 2007, 5 pages.
International Search Report dated Dec. 11, 2007, for PCT Patent Application No. PCT/US2007/012358, filed on May 21, 2007, 3 pages.
International Search Report dated Jan. 28, 2008, for PCT Patent Application No. PCT/US2007/012189, filed on May 21, 2007, 2 pages.
International Search Report dated Oct. 23, 2008, for PCT Patent Application No. PCT/US2008/069435, filed on Jul. 8, 2008, 4 pages.
International Search Report dated Feb. 25, 2009, for PCT Patent Application No. PCT/US2008/071390, filed on Jul. 28, 2008, 2 pages.
International Search Report dated Mar. 13, 2009, for PCT Patent Application No. PCT/US2008/083034, filed on Nov. 10, 2008, 3 pages.
International Search Report dated Mar. 13, 2009, for PCT Patent Application No. PCT/US2008/079891, filed on Nov. 10, 2008, 2 pages.
International Search Report dated Apr. 6, 2009, for PCT Patent Application No. PCT/US2008/079878, filed on Oct. 14, 2008, 3 pages.
Invitation to Pay Additional Fees dated Jul. 6, 2007, for PCT Patent Application No. PCT/US2007/002096, filed on Jan. 23, 2007, 4 pages.
Invitation to Pay Additional Fees dated Aug. 7, 2007, for PCT Patent Application No. PCT/US2007/003322, filed on Feb. 6, 2007, 5 pages.
Invitation to Pay Additional Fees dated Aug. 7, 2007, for PCT Patent Application No. PCT/US2007/003631, filed on Feb. 9, 2007, 5 pages.
Invitation to Pay Additional Fees dated Nov. 11, 2008, for PCT Patent Application No. PCT/US2008/071390, filed on Jul. 28, 2008, 5 pages.
Invitation to Pay Additional Fees dated Dec. 29, 2008, for PCT Patent Application No. PCT/US2008/079891, filed on Oct. 14, 2008, 7 pages.
Japanese Office Action dated Jul. 19, 2011, for Japanese Patent Application No. 2007-550378, filed on Dec. 8, 2005, with English Translation, 11 pages.
Japanese Office Action dated Feb. 28, 2012, for Japanese Patent Application No. 2008-545817, filed on Dec. 13, 2006, with English Translation, 6 pages.
Japanese Office Action dated Jan. 8, 2013 for Japanese Patent Application No. 2008-545817, filed on Dec. 13, 2006, with English Translation, 6 pages.
Japanese Office Action dated Feb. 28, 2012, for Japanese Patent Application No. 2008-551487, filed on Jan. 23, 2007, with English Translation, 9 pages.
Japanese Office Action dated Feb. 28, 2012, for Japanese Patent Application No. 2008-554410, filed on Feb. 9, 2007, 6 pages.
Japanese Office Action dated Mar. 6, 2012, for Japanese Patent Application No. 2008-553430, filed on Feb. 6, 2007, with English Translation, 6 pages.
Japanese Office Action dated Mar. 5, 2013, for Japanese Patent Application No. 2008-553430, filed on Feb. 6, 2007, with English Translation, 6 pages.
Non-Final Office Action dated Jan. 10, 2008, for U.S. Appl. No. 11/160,646, filed Jul. 1, 2005, 6 pages.
Non-Final Office Action dated Mar. 12, 2008, for U.S. Appl. No. 11/153,007, filed Jun. 14, 2005, 11 pages.
Non-Final Office Action dated Mar. 25, 2009, for U.S. Appl. No. 11/215,660, filed Aug. 29, 2005, 11 pages.
Non-Final Office Action dated Mar. 29, 2010, for U.S. Appl. No. 11/215,660, filed Aug. 29, 2005, 16 pages.
Non-Final Office Action dated Apr. 6, 2010, for U.S. Appl. No. 11/609,838, filed Dec. 12, 2006, 25 pages.
Non-Final Office Action dated Aug. 24, 2010, for U.S. Appl. No. 11/834,540, filed Aug. 6, 2007, 11 pages.
Non-Final Office Action dated Oct. 18, 2010, for U.S. Appl. No. 11/626,189, filed Jan. 23, 2007, 11 pages.
Non-Final Office Action dated Oct. 28, 2010, for U.S. Appl. No. 11/828,835, filed Jul. 26, 2007, 11 pages.
Non-Final Office Action dated Dec. 22, 2010, for U.S. Appl. No. 11/751,605, filed May 21, 2007, 10 pages.
Non-Final Office Action dated Feb. 17, 2011, for U.S. Appl. No. 11/609,838, filed Dec. 12, 2006, 24 pages.
Non-Final Office Action dated Mar. 2, 2011, for U.S. Appl. No. 11/736,438, filed Apr. 17, 2007, 10 pages.
Non-Final Office Action dated May 23, 2011, for U.S. Appl. No. 12/101,050, filed Apr. 10, 2008, 11 pages.
Non-Final Office Action dated Jun. 28, 2011, for U.S. Appl. No. 11/938,256, filed Nov. 10, 2007, 23 pages.
Non-Final Office Action dated Aug. 4, 2011, for U.S. Appl. No. 11/609,838, filed Dec. 12, 2006, 16 pages.
Non-Final Office Action dated Aug. 15, 2011, for U.S. Appl. No. 11/626,189, filed Jan. 23, 2007, 13 pages.
Non-Final Office Action dated Aug. 18, 2011, for U.S. Appl. No. 11/751,597, filed May 21, 2007, 25 pages.
Non-Final Office Action dated Sep. 9, 2011, for U.S. Appl. No. 11/751,596, filed May 21, 2007, 6 pages.
Non-Final Office Action dated Oct. 21, 2011, for U.S. Appl. No. 12/251,406, filed Oct. 14, 2008, 8 pages.
Non-Final Office Action dated Oct. 26, 2011, for U.S. Appl. No. 11/673,470, filed Feb. 9, 2007, 40 pages.

(56) References Cited

OTHER PUBLICATIONS

Non-Final Office Action dated Nov. 23, 2011, for U.S. Appl. No. 11/672,020, filed Feb. 6, 2007, 12 pages.
Non-Final Office Action dated Jun. 22, 2012, for U.S. Appl. No. 12/181,280, filed Jun. 22, 2012, 12 pages.
Non-Final Office Action dated May 14, 2013, for U.S. Appl. No. 11/751,605, filed May 21, 2007, 11 pages.
Notice of Allowance dated Dec. 13, 2010, for U.S. Appl. No. 11/834,540, filed Aug. 6, 2007, 4 pages.
Notice of Allowance dated Jul. 22, 2011, for U.S. Appl. No. 12/101,050, filed Apr. 10, 2008, 7 pages.
Notice of Allowance dated Feb. 8, 2012, for U.S. Appl. No. 11/609,838, filed Dec. 12, 2006, 8 pages.
Notice of Allowance dated Feb. 29, 2012, for U.S. Appl. No. 11/751,596, filed May 21, 2007, 10 pages.
Notice of Allowance dated Mar. 14, 2012, for U.S. Appl. No. 11/626,189, filed Jan. 23, 2007, 13 pages.
Notice of Allowance dated Jun. 7, 2012, for U.S. Appl. No. 11/751,597, filed May 21, 2007, 17 pages.
Preliminary Amendment filed Jan. 26, 2009, for U.S. Appl. No. 11/672,020, filed Feb. 6, 2007, filed Feb. 6, 2007, 11 pages.
Response to European Communication filed Feb. 6, 2009, for European Patent Application No. 07777255.6, filed on May 21, 2007, 5 pages.
Response to European Office Action filed on Nov. 11, 2009, for European Patent Application No. 07783368.3, filed on Feb. 6, 2007, 12 pages.
Response to European Office Action filed on Jul. 7, 2010, for European Patent Application No. 06845440.4, filed on Dec. 13, 2006, 13 pages.
Response to European Office Action filed on Aug. 18, 2010, for European Patent Application No. 07717235.1, filed on Feb. 9, 2007, 7 pages.
Response to European Office Action filed on Mar. 8, 2011, for European Patent Application No. 05854262.2, filed on Dec. 8, 2005, 11 pages.
Response to European Office Action filed on Dec. 13, 2011, for European Patent Application No. 07795177.0, filed on May 21, 2007, 9 pages.
Restriction Requirement dated Jun. 21, 2013, for U.S. Appl. No. 13/454,974, filed Apr. 24, 2012, 11 pages.
Response to Restriction Requirement filed on Jan. 26, 2009, for U.S. Appl. No. 11/215,660, filed Aug. 29, 2005, 2 pages.
Response to Restriction Requirement filed on Jul. 23, 2010, for U.S. Appl. No. 11/751,605, filed May 21, 2007, 9 pages.
Response to Restriction Requirement filed on Aug. 4, 2010, for U.S. Appl. No. 11/834,540, filed Aug. 6, 2007, 5 pages.
Response to Restriction Requirement filed on Sep. 9, 2010, for U.S. Appl. No. 11/626,189, filed Jan. 23, 2007, 8 pages.
Response to Restriction Requirement filed on Oct. 21, 2010, for U.S. Appl. No. 11/828,835, filed Jul. 26, 2007, 7 pages.
Response to Restriction Requirement filed on Feb. 8, 2011, for U.S. Appl. No. 11/736,438, filed Apr. 17, 2007, 8 pages.
Response to Restriction Requirement filed on Apr. 27, 2011, for U.S. Appl. No. 12/101,050, filed Apr. 10, 2008, 11 pages.
Response to Restriction Requirement filed on Jun. 16, 2011, for U.S. Appl. No. 11/751,596, filed May 21, 2007, 8 pages.
Response to Restriction Requirement filed on Oct. 31, 2011, for U.S. Appl. No. 11/672,020, filed Feb. 6, 2007, 3 pages.
Restriction Requirement dated Oct. 30, 2008, for U.S. Appl. No. 11/215,660, filed Aug. 29, 2005, 7 pages.
Restriction Requirement dated Jun. 25, 2010, for U.S. Appl. No. 11/751,605, filed May 21, 2007, 9 pages.
Restriction Requirement dated Jul. 13, 2010, for U.S. Appl. No. 11/834,540, filed Aug. 6, 2007, 8 pages.
Restriction Requirement dated Aug. 10, 2010, for U.S. Appl. No. 11/626,189, filed Jan. 23, 2007, 5 pages.
Restriction Requirement dated Sep. 21, 2010, for U.S. Appl. No. 11/828,835, filed Jul. 26, 2007, 6 pages.
Restriction Requirement dated Dec. 10, 2010, for U.S. Appl. No. 11/736,438, filed Apr. 17, 2007, 16 pages.
Restriction Requirement dated Mar. 11, 2011, for U.S. Appl. No. 12/101,050, filed Apr. 10, 2008, 6 pages.
Restriction Requirement dated Jun. 6, 2011, for U.S. Appl. No. 11/751,596, filed May 21, 2007, 6 pages.
Restriction Requirement dated Sep. 29, 2011, for U.S. Appl. No. 11/672,020, filed Feb. 6, 2007, 6 pages.
Restriction Requirement dated Nov. 28, 2011, for U.S. Appl. No. 12/251,383, filed Oct. 14, 2008, 6 pages.
Substitute Preliminary Amendment filed Mar. 8, 2010, for U.S. Appl. No. 11/672,020, filed Feb. 6, 2007, 2 pages.
Written Opinion of the International Searching Authority dated May 18, 2006, for PCT Patent Application No. PCT/US2005/045499, filed on Dec. 8, 2005, 9 pages.
Written Opinion of the International Searching Authority dated May 19, 2006, for PCT Patent Application No. PCT/US2005/044624, filed on Dec. 8, 2005, 8 pages.
Written Opinion of the International Searching Authority dated Jun. 20, 2007, for PCT Patent Application No. PCT/US2006/047748, filed on Dec. 13, 2006, 7 pages.
Written Opinion of the International Searching Authority dated Sep. 28, 2007, for PCT Patent Application No. PCT/US2007/002096 filed on Jan. 23, 2007, 8 pages.
Written Opinion of the International Searching Authority dated Oct. 25, 2007, for PCT Patent Application No. PCT/US2007/003322, filed on Feb. 6, 2007, 9 pages.
Written Opinion of the International Searching Authority dated Oct. 26, 2007, for PCT Patent Application No. PCT/US2007/003631, filed on Feb. 9, 2007, 7 pages.
Written Opinion of the International Searching Authority dated Dec. 11, 2007, for PCT Patent Application No. PCT/US2007/012358, filed on May 21, 2007, 6 pages.
Written Opinion of the International Searching Authority dated Jan. 28, 2008, for PCT Patent Application No. PCT/US2007/012189, filed on May 21, 2007, 7 pages.
Written Opinion of the International Searching Authority dated Oct. 23, 2008, for PCT Patent Application No. PCT/US2008/069435, filed on Jul. 8, 2008, 6 pages.
Written Opinion of the International Searching Authority dated Feb. 25, 2009, for PCT Patent Application No. PCT/US2008/071390, filed on Jul. 28, 2008, 7 pages.
Written Opinion of the International Searching Authority dated Mar. 13, 2009, for PCT Patent Application No. PCT/US2008/083034, filed on Nov. 10, 2008, 4 pages.
Written Opinion of International Searching Authority dated Mar. 13, 2009, for PCT Patent Application No. PCT/US2008/079891, filed on Nov. 10, 2008, 5 pages.
Written Opinion of International Searching Authority dated Apr. 6, 2009, for PCT Patent Application No. PCT/US2008/079878, filed on Oct. 14, 2008, 13 pages.
Intention to Grant Received for European Patent Application No. 07795177.0, dated Jul. 10, 2014, 7 pages.
Office Action received for Japanese Patent Application No. 2013-111118, dated Apr. 28, 2015, 7 pages (4 pages of English Translation and 3 pages of JPOA).
International Preliminary Report on Patentability received for PCT Patent Application No. PCT/US2005/045499, dated Jul. 10, 2007, 10 pages.
International Preliminary Report on Patentability received for PCT Patent Application No. PCT/US2006/047748, dated Jun. 18, 2008, 8 pages.
International Preliminary Report on Patentability received for PCT Patent Application No. PCT/US2007/002096, dated Jul. 29, 2008, 9 pages.
International Preliminary Report on Patentability received for PCT Patent Application No. PCT/US2007/003322, dated Aug. 12, 2008, 10 pages.
International Preliminary Report on Patentability received for PCT Patent Application No. PCT/US2007/003631, dated Aug. 12, 2008, 8 pages.

(56) References Cited

OTHER PUBLICATIONS

International Preliminary Report on Patentability received for PCT Patent Application No. PCT/US2007/012189, dated Nov. 21, 2008, 8 pages.
International Preliminary Report on Patentability received for PCT Patent Application No. PCT/US2007/012358, dated Nov. 21, 2008, 7 pages.
International Preliminary Report on Patentability received for PCT Patent Application No. PCT/US2008/069435, dated Jan. 26, 2010, 7 pages.
International Preliminary Report on Patentability received for PCT Patent Application No. PCT/US2008/071390, dated Jan. 26, 2010, 8 pages.
International Preliminary Report on Patentability received for PCT Patent Application No. PCT/US2008/079878, dated Apr. 13, 2010, 14 pages.
International Preliminary Report on Patentability received for PCT Patent Application No. PCT/US2008/079891, dated Apr. 13, 2010, 6 pages.
International Preliminary Report on Patentability received for PCT Patent Application No. PCT/US2008/083034, dated May 11, 2010, 5 pages.
Extended European Search Report received for European Patent Application No. 12153947.2, dated Apr. 26, 2012, 6 pages.
Office Action received for European Patent Application No. 05854262.2, dated Nov. 6, 2007, 2 pages.
Office Action received for European Patent Application No. 05854262.2, dated Sep. 3, 2013, 6 pages.
Office Action received for European Patent Application No. 07717024.9, dated Mar. 6, 2009, 2 pages.
Office Action received for Japanese Patent Application No. 2010-518438, dated Jan. 15, 2013.
Office Action Received for Japanese Patent Application No. 2013-111118, dated May 27, 2014, 13 pages.
Office Action Received for Japanese Patent Application No. 2013-138949, dated May 13, 2014, 6 pages.
Notice of Allowance received for U.S. Appl. No. 11/672,020, dated Jun. 19, 2012, 10 pages.
Non-Final Office Action received for U.S. Appl. No. 12/251,383, dated Feb. 14, 2012, 10 pages.
Non-Final Office Action received for U.S. Appl. No. 13/275,206, dated Feb. 13, 2012, 14 pages.
Non-Final Office Action received for U.S. Appl. No. 13/042,656, dated Jul. 12, 2012, 5 pages.
Notice of Allowance received for U.S. Appl. No. 13/606,465, dated Jul. 19, 2013, 15 pages.
Non-Final Office Action received for U.S. Appl. No. 11/215,660, dated Nov. 14, 2013, 11 pages.
Final Office Action received for U.S. Appl. No. 11/215,660, dated Jun. 10, 2014, 15 pages.
Non-Final Office Action received for U.S. Appl. No. 11/673,470, dated Aug. 30, 2013, 37 pages.
Notice of Allowance received for U.S. Appl. No. 11/673,470 dated Jun. 23, 2014, 9 pages.
Final Office Action received for U.S. Appl. No. 11/751,605, dated Mar. 6, 2014, 9 pages.
Notice of Allowance received for U.S. Appl. No. 11/751,605, dated Oct. 1, 2014, 7 pages.
Non-Final Office Action received for U.S. Appl. No. 11/828,835, dated Jul. 10, 2014, 14 pages.
Non-Final Office Action received for U.S. Appl. No. 11/938,256, dated Jul. 19, 2013, 13 pages.
Notice of Allowance received for U.S. Appl. No. 11/938,256, dated Mar. 3, 2014, 5 pages.
Non-Final Office Action received for U.S. Appl. No. 13/346,578, dated Dec. 29, 2014, 17 pages.
Final Office Action received for U.S. Appl. No. 13/454,974, dated Jul. 7, 2014, 12 pages.
Non-Final Office Action received for U.S. Appl. No. 13/454,974, dated Jan. 26, 2015, 14 pages.
Non-Final Office Action received for U.S. Appl. No. 13/454,974, dated Sep. 5, 2013, 12 pages.
Non-Final Office Action received for U.S. Appl. No. 13/467,909, dated Oct. 22, 2014, 9 pages.
Non-Final Office Action received for U.S. Appl. No. 13/584,647, dated Sep. 20, 2013, 14 pages.
Final Office Action received for U.S. Appl. No. 13/584,647, dated Apr. 16, 2014, 15 pages.
Non-Final Office Action received for U.S. Appl. No. 13/584,647, dated Sep. 25, 2014, 16 pages.
Notice of Allowance received for U.S. Appl. No. 13/584,647, dated Mar. 10, 2015, 9 pages.
Non-Final Office Action received for U.S. Appl. No. 14/025,539, dated Dec. 22, 2014, 13 pages.
Notice of Allowance received for U.S. Appl. No. 14/056,741, dated Dec. 19, 2014, 10 pages.
Final Office Action Received for U.S. Appl. No. 13/467,909, dated Jun. 19, 2015, 8 pages.
Decision to Grant received for European Patent Application No. 07763368.3, dated Oct. 25, 2012, 2 pages.
Intention to Grant received for European Patent Application No. 07763368.3, dated Jun. 13, 2012, 8 pages.
Advisory Action received for U.S. Appl. No. 13/454,974, dated Oct. 6, 2014, 3 pages.
Final Office Action received for U.S. Appl. No. 13/454,974, dated Sep. 24, 2015, 17 pages.
Non-Final Office Action received for U.S. Appl. No. 13/467,909, dated Mar. 9, 2016, 11 pages.
Final Office Action received for U.S. Appl. No. 14/025,539, dated Sep. 28, 2015, 12 pages.
Non Final Office Action received for U.S. Appl. No. 14/694,968, dated Jan. 4, 2016, 10 pages.
Final Office Action dated Nov. 17, 2016, for U.S. Appl. No. 13/467,909, filed May 9, 2012, 12 pages.
International Search Report dated Oct. 10, 2014, for PCT Patent Application No. PCT/US2014/038506, filed on May 16, 2014, 2 pages.
Non-Final Office Action dated Jul. 29, 2016, for U.S. Appl. No. 14/338,247, filed Jul. 22, 2014, 8 pages.
Notice of Allowance dated Jun. 26, 2012, for U.S. Appl. No. 11/736,438, filed Apr. 17, 2007, 10 pages.
Notice of Allowance dated Nov. 23, 2016, for U.S. Appl. No. 14/701,372, filed Apr. 30, 2015, 12 pages.
Written Opinion of the International Searching Authority dated Oct. 10, 2014, for PCT Patent Application No. PCT/US2014/038506, filed on May 16, 2014, 7 pages.
Non-Final Office Action dated Jan. 18, 2017, for U.S. Appl. No. 13/454,974, filed Apr. 24, 2012, 9 pages.
Non-Final Office Action dated Feb. 9, 2017, for U.S. Appl. No. 14/280,469, filed May 16, 2014, 12 pages.
Non-Final Office Action dated Jun. 29, 2017, for U.S. Appl. No. 13/467,909, filed May 9, 2012, 10 pages.

* cited by examiner

ENDOSCOPE

CROSS-REFERENCE TO RELATED APPLICATIONS

This application is a continuation application of U.S. patent application Ser. No. 11/626,189, filed Jan. 23, 2007, now issued as U.S. Pat. No. 8,235,887, which claims the benefit of U.S. Provisional Patent Application No. 60/761,475, filed Jan. 23, 2006, the entire disclosures of which are incorporated herein by reference.

U.S. patent application Ser. No. 11/626,189, filed Jan. 23, 2007, now issued as U.S. Pat. No. 8,235,887, additionally claims the benefit of U.S. Provisional Patent Application No. 60/802,056, filed May 19, 2006, the entire disclosure of which is incorporated herein by reference.

The entire disclosure of U.S. patent application Ser. No. 11/609,838, filed Dec. 12, 2006 is incorporated herein by reference.

The entire disclosure of U.S. patent application Ser. No. 11/609,660, filed Aug. 29, 2005, is incorporated herein by reference.

TECHNICAL FIELD OF THE INVENTION

The present invention relates to an endoscope.

BACKGROUND OF THE INVENTION

An endoscope is a medical device comprising a flexible tube and a camera mounted on the distal end of the tube. The endoscope is insertable into an internal body cavity through a body orifice to examine the body cavity and tissues for diagnosis. The tube of the endoscope has one or more longitudinal channels, through which an instrument can reach the body cavity to take samples of suspicious tissues or to perform other surgical procedures such as polypectomy.

There are many types of endoscopes, and they are named in relation to the organs or areas with which they are used. For example, gastroscopes are used for examination and treatment of the esophagus, stomach and duodenum; colonoscopes for the colon; bronchoscopes for the bronchi; laparoscopes for the peritoneal cavity; sigmoidoscopes for the rectum and the sigmoid colon; arthroscopes for joints; cystoscopes for the urinary bladder; and angioscopes for the examination of blood vessels.

Each endoscope has a single forward viewing camera mounted at the distal end of the endoscope to transmit an image to an eyepiece or video display at the proximal end. The camera is used to assist a medical professional in advancing the endoscope into a body cavity and looking for abnormalities. The camera provides the medical professional with a two-dimensional view from the distal end of the endoscope. To capture an image from a different angle or in a different portion, the endoscope must be repositioned or moved back and forth. Repositioning and movement of the endoscope prolongs the procedure and causes added discomfort, complications, and risks to the patient. Additionally, in an environment such as the lower gastro-intestinal tract, flexures, tissue folds and unusual geometries of the organ may prevent the endoscope's camera from viewing all areas of the organ. The unseen area may cause a potentially malignant (cancerous) polyp to be missed.

This problem can be overcome by providing an auxiliary camera, which presents an image of the areas not viewable by the endoscope's main camera. The auxiliary camera can be oriented backwards to face the main camera. This arrangement of cameras can provide both front and rear views of an area or an abnormality. In the case of polypectomy where a polyp is excised by placing a wire loop around the base of the polyp, the camera arrangement allows better placement of the wire loop to minimize damage to the adjacent healthy tissue.

SUMMARY OF THE INVENTION

The present invention provides endoscopes that have various advantages over the prior art. According to one aspect of the present invention, an endoscope includes an insertion tube that has a distal end, and an imaging device that includes a steerable extension with a distal end and a proximal end. The proximal end of the extension is attached to the distal end of the insertion tube.

The distal end of the steerable extension may be steered in various manners. For example, the distal end of the steerable extension may be steered in one direction up to 180°. Alternatively, the distal end of the steerable extension may be steered up to 180° in any one of two opposite directions. In some cases, the distal end of the steerable extension is steered in three or more directions.

In a preferred embodiment, the steerable extension has a diameter that is approximately a third of the insertion tube's diameter.

In another preferred embodiment, the imaging device includes an imaging unit that is provided on the distal end of the steerable extension. Additionally or alternatively, the imaging unit may be provided on a cylindrical side surface of the distal end region of the steerable extension. Furthermore, two imaging units may be provided on the opposite sides of the distal end region of the steerable extension.

The steerable imaging device according to this aspect of the invention allows a physician to better locate the imaging device, resulting in a greater viewing field and allowing viewing of the areas behind folds and flexures. The steerable imaging device is advantageous also because it allows a greater degree of movement due to its smaller diameter and greater flexibility as compared to an imaging device mounted on the distal end of the insertion tube.

In accordance with another aspect of the invention, an endoscope includes an insertion tube having a distal end region, and a rear-viewing imaging device that is at least partially disposed inside the distal end region. The insertion tube may have a sheath with a window placed in front of the rear-viewing imaging device to allow the imaging device to "see" an object outside of the insertion tube. Alternatively, the rear-viewing imaging device may protrude outside of the insertion tube so that a window is not needed.

In a preferred embodiment, the distal end region of the insertion tube may include a circular groove having a front-facing sidewall and a rear-facing sidewall. The rear-facing sidewall has a window placed in front of the rear-viewing imaging device. Alternatively, the rear-viewing imaging device may protrude outside of the rear-facing sidewall so that a window is not needed. The groove of this embodiment provides the imaging device with a better field of view.

In another preferred embodiment, the distal end region of the insertion tube includes a circular protrusion having a front-facing side and a rear-facing side. The rear-facing side of the protrusion has a window placed in front of the rear-viewing imaging device. Alternatively, the rear-viewing imaging device protrudes outside of the rear-facing side of the protrusion so that a window is not needed. The circular protrusion of this embodiment provides the imaging device with a better field of view.

In a further embodiment of the invention, the endoscope includes a plurality of rear-viewing imaging devices, wherein the image signals from the rear-viewing imaging devices are combined to provide a 360° rear view.

In accordance with a still further aspect of the invention, an endoscope includes an insertion tube having a distal end cap, an imaging device, and a link that couples the imaging device to the distal end cap of the insertion tube. The imaging device may include a housing element, and the housing element, link and distal end cap may form a unitary unit. In a preferred embodiment, the endoscope further comprises a main imaging device positioned on a distal end of the insertion tube, wherein the two imaging devices provide different views of the same area.

DETAILED DESCRIPTION OF EMBODIMENTS OF THE INVENTION

Figure 1:
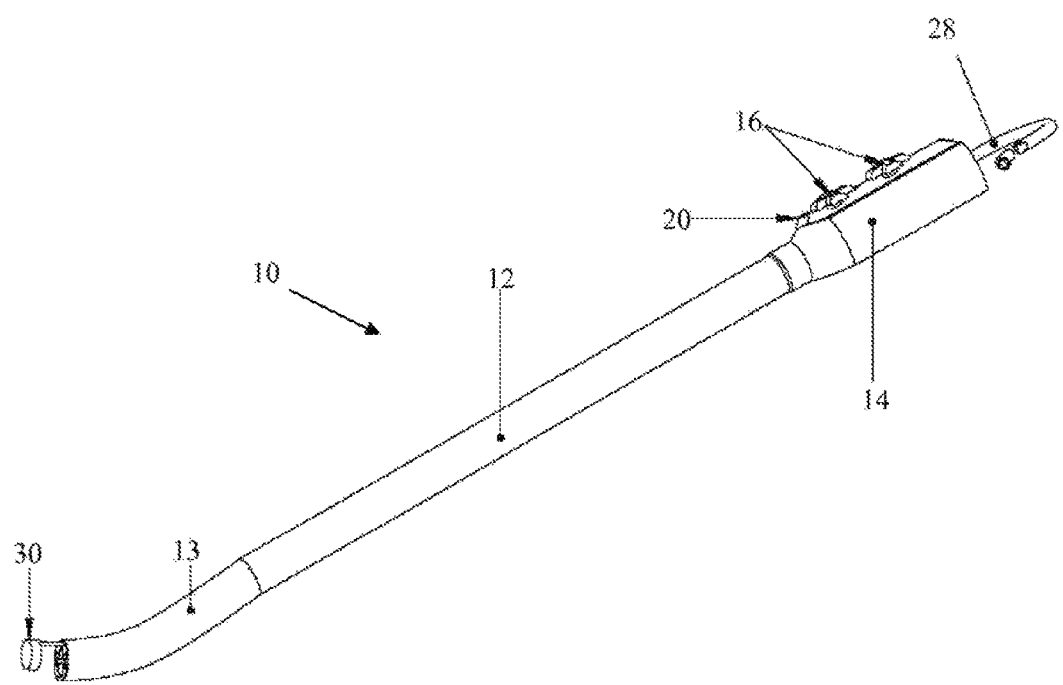
FIG. 1 shows a perspective view of an endoscope according to one embodiment of the present invention.

FIG. 1 illustrates a first exemplary endoscope 10 of the present invention. This endoscope 10 can be used in a variety of medical procedures in which imaging of a body tissue, organ, cavity or lumen is required. The types of procedures include, for example, anoscopy, arthroscopy, bronchoscopy, colonoscopy, cystoscopy, EGD, laparoscopy, and sigmoidoscopy.

The endoscope 10 of FIG. 1 may include an insertion tube 12 having a main imaging device 26 at its distal end (FIG. 2), a control handle 14 connected to the insertion tube 12, and a secondary imaging device 30 positioned at the distal end of the endoscope 10.

The insertion tube 12 of the endoscope 10 may be detachable from the control handle 14 or may be integrally formed with the control handle 14. The diameter, length and flexibility of the insertion tube 12 depend on the procedure for which the endoscope 10 is used.

Figure 2:
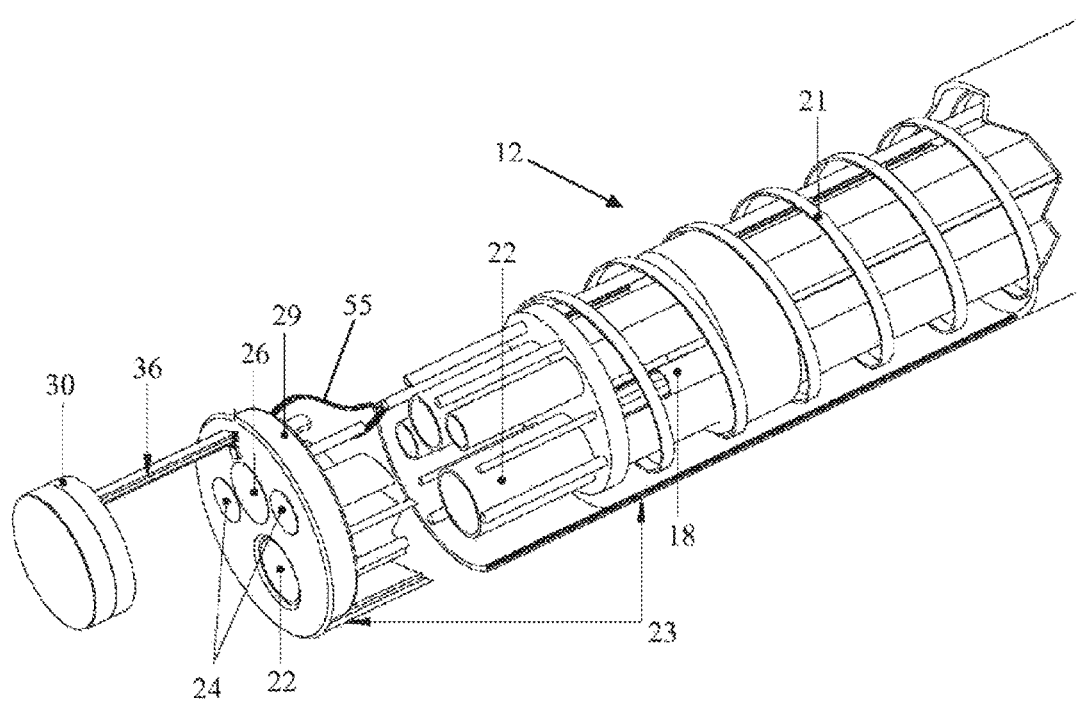
FIG. 2 shows a perspective cutaway view of the endoscope of FIG. 1.

As shown in FIG. 2, the insertion tube 12 preferably has one or more longitudinal channels 22 through which an instrument can reach the body cavity to perform any desired procedures, such as to take samples of suspicious tissues or to perform other surgical procedures such as polypectomy. The instruments may be, for example, a retractable needle for drug injection, hydraulically actuated scissors, clamps, grasping tools, electrocoagulation systems, ultrasound transducers, electrical sensors, heating elements, laser mechanisms and other ablation means. In some embodiments, one of the channels 22 can be used to supply a washing liquid such as water for washing. A cap (not shown) may be included at the opening of the washing channel 22 to divert the washing liquid onto a lens of the main imaging device 26 for cleaning. Another or the same channel 22 may be used to supply a gas, such as $CO_2$ or air into the organ. The channels 22 may also be used to extract fluids or inject fluids, such as a drug in a liquid carrier, into the body. Various biopsy, drug delivery, and other diagnostic and therapeutic devices may also be inserted via the channels 22 to perform specific functions.

The insertion tube 12 preferably is steerable or has a steerable distal end region 13 (FIG. 1). The length of the distal end region 13 may be any suitable fraction of the length of the insertion tube 12, such as one half, one third, one fourth, one sixth, one tenth, or one twentieth. The insertion tube 12 may have control cables 18 (FIG. 2) for the manipulation of the insertion tube 12. Preferably, the control cables 18 are symmetrically positioned within the insertion tube 12 and extend along the length of the insertion tube 12. The control cables 18 may be anchored at or near the distal end of the insertion tube 12. Each of the control cables 18 may be a Bowden cable, which includes a wire contained in a flexible overlying hollow tube. The wires of the Bowden cables are attached to controls (not shown) in the handle 14. Using the controls, the wires can be pulled to bend the distal end region 13 of the insertion tube 12 in a given direction. The Bowden cables can be used to articulate the distal end region of the insertion tube 12 in different directions.

The main imaging device 26 at the distal end of the insertion tube 12 may include, for example, a lens, single chip sensor, multiple chip sensor or fiber optic implemented devices. The main imaging device 26, in electrical communication with a processor and/or monitor, may provide still images or recorded or live video images. In addition to the main imaging device 26, the distal end of the insertion tube 12 may include one or more light sources 24, such as light emitting diodes (LEDs) or fiber optical delivery of light from an external light source. The light sources 24 preferably are equidistant from the main imaging device 26 to provide even illumination. Each light source 24, individually, can be turned on or off. The intensity of each light source 24 can be adjusted to achieve optimum imaging. The circuits for the main imaging device 26 and light sources 24 may be incorporated into a printed circuit board (PCB) 27 (FIG. 3), which can be mounted on the proximal side of an end cap 29 of the insertion tube 12.

As shown in FIG. 2, the insertion tube 12 may include a flexible ribbon coil 21 and a flexible sheath 23 that is used to protect the internal components of the insertion tube 12, such as the channels 22, wires and cables 25, from the environment of the body. The end cap 29 of the insertion tube 12 seals the open end of the shield 23 to close the distal end of the insertion tube 12. The end cap 29 includes an exit port for the channel 22 and peripheral metal posts or sockets (not shown) to which the wires of the control cables 18 are attached.

As shown in FIG. 1, the control handle 14 may include one or more control knobs 16 that are attached to control cables 18 (FIG. 2) for the manipulation of the insertion tube 12. Preferably, the rotation of the control knobs 16 pulls the control cables 18 and therefore moves or bends the distal end region 13 of the insertion tube 12 up and down and/or side to side. In some embodiments, a clutch or breaking component (not shown) may be included with the control knobs 16 to prevent the knobs 16 from being inadvertently rotated such that rotation can only be caused by application of a certain degree of torque to the control knobs 16.

Preferably, as shown in FIG. 1, the control handle 14 has one or more ports and/or valves 20 for controlling access to the channels 22 (FIG. 2) of the insertion tube 12. The ports and/or valves 20 can be air or water valves, suction valves, instrumentation ports, and suction/instrumentation ports.

Additionally, the control handle 14 may include buttons for taking pictures with the main imaging device 26, the secondary imaging device 30, or both.

The proximal end of the control handle 14 may include an accessory outlet 28 (FIG. 1) that provides fluid communication between the air, water and suction channels and the pumps and related accessories. The same outlet or a different outlet can be used for electrical lines to light and imaging components at the distal end of the endoscope 10.

As illustrated in FIG. 2, a link 36 is used to connect the secondary imaging device 30 to the end cap 29 of the insertion tube 12. In the illustrated embodiment, the link 36 is a generally elongated, flat, straight bar, although the link may be configured in any suitable manner. For example, the link may be curved and may have a circular or square cross-section. The link may comprise one pole, as shown in FIG. 2, or two or more poles to enhance support to the secondary imaging device 30. In some embodiments, the link may be made from a transparent material, and the transparent link may be a transparent tube connected to the circumferences of the secondary imaging device 30 and end cap 29. Preferably, the link 36 is suitably flexible to make it easier for the secondary imaging device 30 to negotiate and accommodate the flexures along the body cavity.

Figure 3:
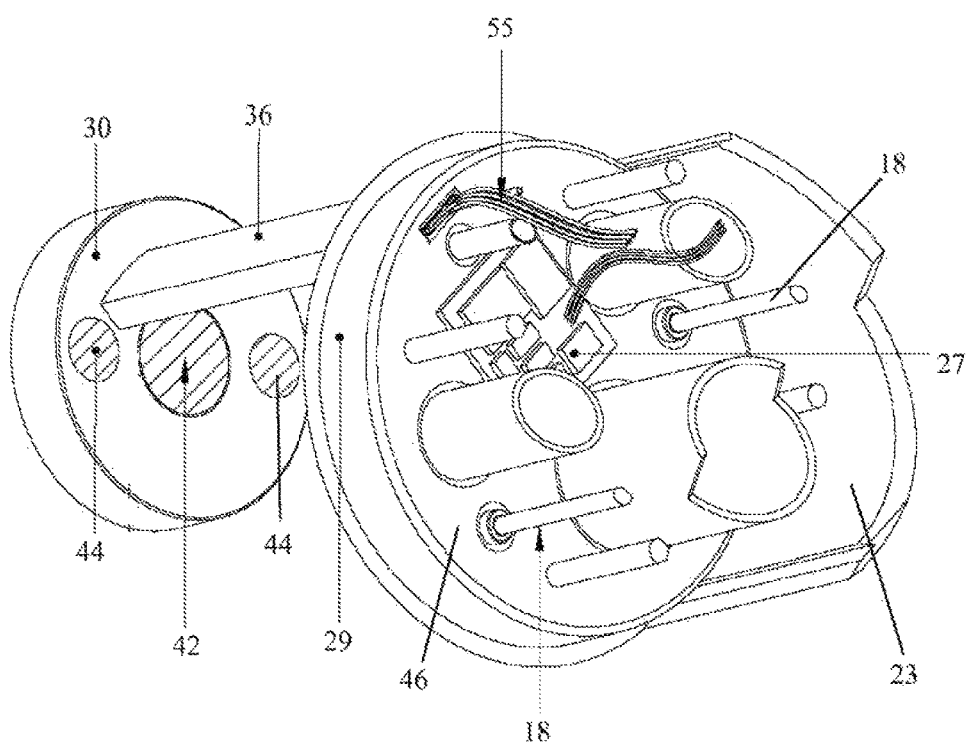
FIG. 3 shows another perspective cutaway view of the endoscope of FIG. 1.

Preferably, the secondary imaging device 30 has an imaging unit 42 and one or more light sources 44 such as LEDs, as shown in FIG. 3. In this embodiment, the imaging unit 42 and light sources 44 are placed on the proximal end 46 of the secondary imaging device 30, although they may be placed at any suitable locations on the secondary imaging device 30, including on the distal end or side of the secondary imaging device 30 or both. Preferably, the imaging unit 42 faces backwards towards the main imaging device 26 and is oriented so that the imaging unit 42 and the main imaging device 26 can be used to provide different views of the same area. In the illustrated embodiment, the imaging unit 42 provides a retrograde view of the area, while the main imaging device 26 provides a front view of the area.

Since the main imaging device 26 and the imaging unit 42 of the secondary imaging device 30 face each other, the light sources 24, 44 of one imaging device 26, 30 may interfere with the other imaging device 30, 26. To reduce the interference, polarizer filters may be used with the imaging devices 26, 30 and light sources 24, 44. The main imaging device 26 and its light sources 24 may be covered by a first set of polarizer filters of the same orientation. And the imaging unit 42 and light source 44 may be covered by a second set of polarizer filters orientated at 90° relative to the first set of polarizer filters. Alternatively, only one of the imaging devices 26, 30 may be covered by a first polarizer filter, and only the opposing light source 24, 44 may be covered by a second polarizer filter orientated at 90° relative to the first polarizer filter. The use of polarizer filters to reduce light interference is well known and will not be described in detail herein.

As an alternative to polarizer filters, the imaging devices 26, 30 and their light sources 24, 44 may be turned on and off alternately to reduce or prevent light interference. In other words, when the main imaging device 26 and its light sources 24 are turned on, the imaging unit 42 and its light sources 44 are turned off. And when the main imaging device 26 and its light sources 24 are turned off, the imaging unit 42 and its light sources 44 are turned on. Preferably, the imaging devices 26, 30 and their light sources 24, 44 are turned on and off at a sufficiently high frequency that eyes do not sense that the light sources are being turned on and off.

Figure 4:
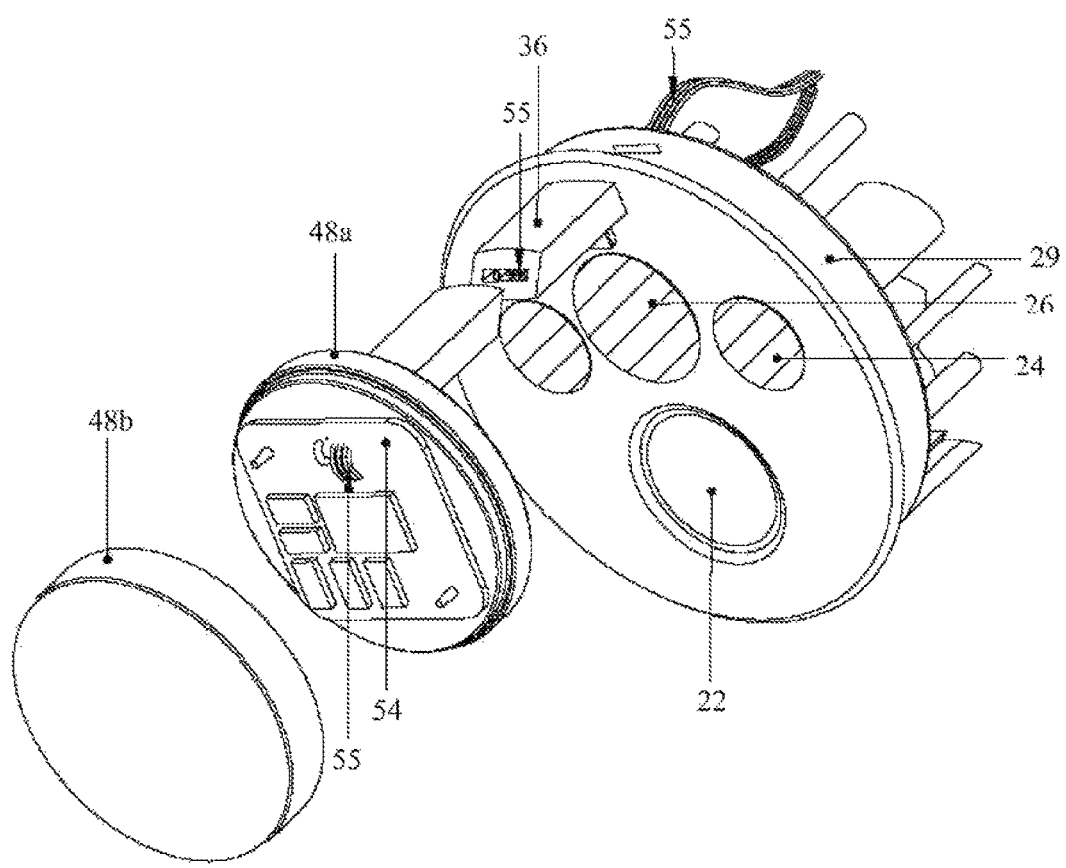
FIG. 4 shows an exploded perspective view of the endoscope of FIG. 1.

As shown in FIG. 4, the secondary imaging device 30 preferably includes a housing 48a, 48b for accommodating the imaging unit 42 and light sources 44. The housing 48a, 48b of the secondary imaging device 30 preferably includes first and second housing elements 48a, 48b. The housing elements 48a, 48b preferably have features, such as pins and sockets, which allow the imaging unit 42 and light source 44 to be securely mounted within the housing elements 48a, 48b. The housing elements 48a, 48b are sealingly attached to each other to maintain biocompatibility of the secondary imaging device 30 and prevent contaminants from entering the secondary imaging device 30. The housing elements 48a, 48b may be sealingly attached to each other in any suitable manner, including ultrasonic or friction welding or adhesive bonding. The housing 48a, 48b may include windows for the imaging unit 42 and light source 44, respectively. Preferably, each window is sealed with a thin clear cover that is attached to the housing 48a, 48b. In some embodiments, the windows may be the polarizer filters described previously.

In a preferred embodiment, the first housing element 48a, the link 36, and the end cap 29 form a unitary unit made by means of, for example, injection molding. The second housing element 48b may be separately formed by means of, for example, injection molding. Preferably, the molded units are fabricated from a biocompatible material such as a biocompatible plastic. Alternatively, the housing elements

48a, 48b, the link 36, and the end cap 29 may be made as separate parts from the same material or different materials and then attached to one another.

As shown in FIG. 4, the circuitry for the imaging unit 42 is formed on a PCB 54. The circuitry for the light sources 44 may also be formed on the same PCB 54. The PCB 54 may additionally include signal processing circuitry and power management circuitry, and can be attached to one of the housing elements 48a by means of, for example, adhesives or screws. The imaging unit 42 may be an electronic device which converts light incident on photosensitive semiconductor elements into electrical signals. Such a device may detect either color or black-and-white image data. The signals from the device are digitized and used to reproduce the image that was incident on the device. Two commonly used types of imaging devices are Charge Coupled Devices (CCD) such as LC 99268 FB produced by Sanyo of Osaka, Japan and Complementary Metal Oxide Semiconductor (CMOS) camera chips such as the OVT 6910 produced by OmniVision of Sunnyvale, Calif.

As shown in FIGS. 2-4, an endoscope 10 may include wires 55 that extend through the like 36, insertion tube 12, and control handle 14 and connect the secondary imaging device 30 to an external control box (not shown). The wires 55 allow the secondary imaging device 30 to communicate with the external control box, including transmitting video signals to the external control box and receiving power and control signals from the external control box.

The image data acquired by the main and secondary imaging devices 26, 30 are transmitted to the external control box for processing. Once received by the external control box, the image signal is fed to a signal processing circuit which converts it to a video signal such as NTSC composite or RGB. This video signal is then sent to a suitable connector for output to a display device such as a monitor or television. In some embodiments, the images from the main imaging device 26 and from the secondary imaging device 30 can be shown together on the same display device with a split screen. The display device may also have a text display area which is used to display patient information or reference number, date, time and other information and also enter notes for still images taken. The text can be typed in by means of a keyboard connected to the control box.

The external control box may also be used as an interface to the patient records database. A large number of medical facilities now make use of electronic medical records. During the procedure relevant video and image data may need to be recorded in the patient electronic medical records (EMR) file. The signal processing circuit can convert image and video data to a format suitable for filing in the patient EMR file such as images in .jpeg, tif, or .bmp format among others. The processed signal can be transmitted to the medical professional's computer or the medical facilities server via a cable or dedicated wireless link. A switch on the control panel can be used to enable this transmission. Alternatively the data can be stored with a unique identification for the patient in electronic memory provided in the control box itself. The signal processing circuit can be utilized to convert the video and image data to be compatible with the electronic medical records system used by the medical professional. The processing may include compression of the data. A cable or a wireless link may be used to transmit the data to a computer.

The image and signal processing circuitry of the external control box includes one or multiple integrated circuits and memory as needed along with associated discrete components. This circuit allows the video signals to be processed for enhancing image quality, enabling still images to be extracted from the video and allow conversion of the video format to provide multiple output formats. These functions can be interfaced for access via the control panel.

The external control box may be used to adjust the parameters of the main and secondary imaging devices 26, 30, such as brightness, exposure time and mode settings. These parameters may be adjusted by writing digital commands to specific registers controlling the parameters. These registers can be addressed by their unique numbers and digital commands can be read from and written to these registers to change the parameters. The control box is used to control these parameters by transmitting data commands to these registers. The signal processing circuit on the secondary imaging device 30 receives and then decodes these signals into commands and feeds them to the image devices 26, 30 to adjust the various parameters.

Figure 5:
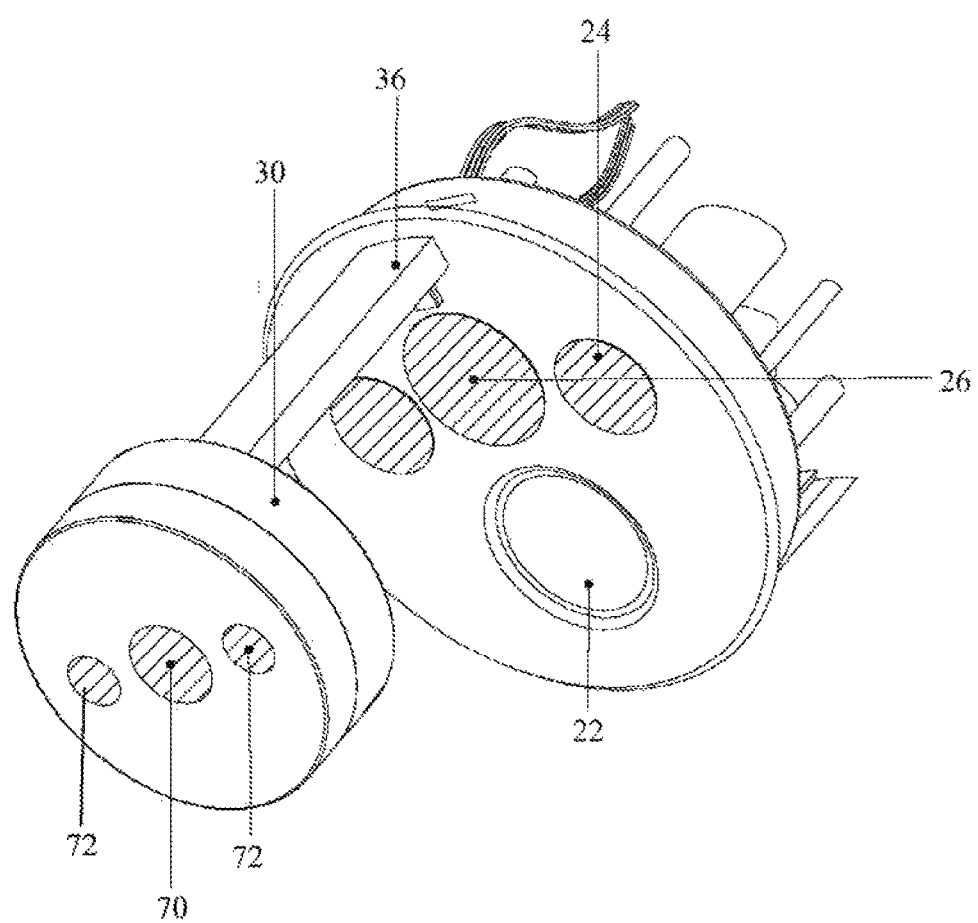
FIG. 5 shows a perspective view of a variation of the endoscope of FIG. 1 with a forward-viewing imaging unit.

The secondary imaging device 30 may additionally include a forward viewing imaging unit 70 and forward facing light sources 72, as shown in FIG. 5. This forward viewing imaging unit 70 allows more effective navigation of the endoscope 10. Additionally, to allow an accessory to reach the area in front of the secondary imaging device 30, the secondary imaging device 30 may be configured so as not to obstruct one or more channels 22 of the insertion tube 12. For example, the secondary imaging device 30 may be made small enough so that it does not obstruct the channel 22 of the insertion tube 12. Alternatively, the secondary imaging device 30 may include a through hole (not shown) aligned with the channel 22 of the insertion tube 12. This through hole allows an accessory to reach the area in front of the secondary imaging device 30.

In accordance with further embodiments of the present invention, the secondary imaging device may have the two imaging units 42, 70, one on the proximal side of the secondary imaging device and the other on the distal side of the secondary imaging device, but the insertion tube 12 does not have the main imaging device 26. The increased space on the distal end of the insertion tube 12 can be used to provide one or more additional channels.

Figure 6:
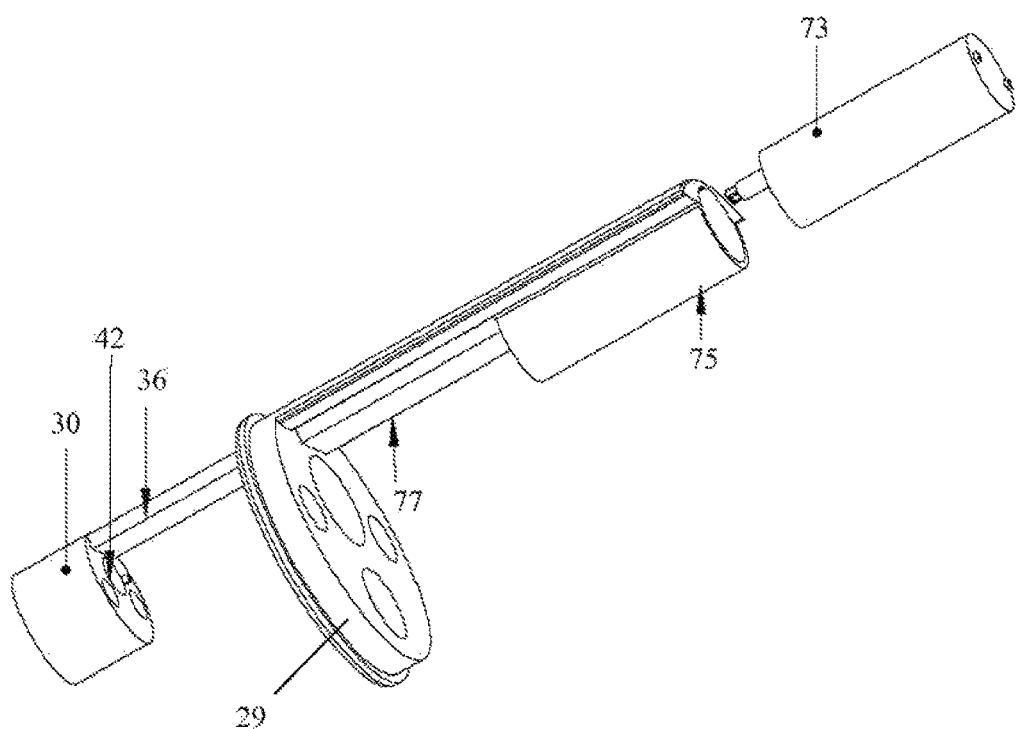
FIG. 6 shows a perspective view of a mechanism for extending a secondary imaging device from, and retracting it into, an insertion tube.

In another embodiment, the secondary imaging device 30 can be extended and retracted from the insertion tube 12. As shown in FIG. 6, the endoscope 10 may include a linear actuator 73 placed in an enclosure 75 and is connected to the link 36. The linear actuator 73 can extend the link 36 from a hollow guide 77 and retract the link 36 into the hollow guide 77. This allows the physician to retract the secondary imaging device 30 when advancing the endoscope 10 through a difficult region of the body, and then extend the secondary imaging device 30 when the endoscope 10 reaches its destination. Additionally, the extension and refraction of the secondary imaging device adjusts the distance between the main and secondary imaging devices.

In operation, the power may be turned on first to activate the imaging devices 26, 30 and the light sources 24, 44. At this point, the imaging devices 26, 30 begin transmitting captured images to the external control box. The control box then processes the image signals and sends them to a display so that a medical professional can visualize the images in real time. At this point, the main imaging device 26 provides a front view of an area, while the secondary imaging device 30 provides a rear or retrograde view of the same area. During the medical procedure, the endoscope 10 is inserted into a patient. The medical professional can simultaneously visualize images from the main imaging device 26 and from the secondary imaging device 30. Lesions hidden from the main imaging device 26 behind folds and flexures can now be viewed by the medical professional from the images provided by the secondary imaging device 30. When the procedure is complete, the endoscope 10 is removed from the patient.

The external control box can be used to adjust the parameters of the imaging devices 26, 30 and light sources 24, 44 to achieve optimum image quality. During the procedure, relevant video and image data may be recorded in the patient's electronic medical records (EMR) file.

Figure 7:
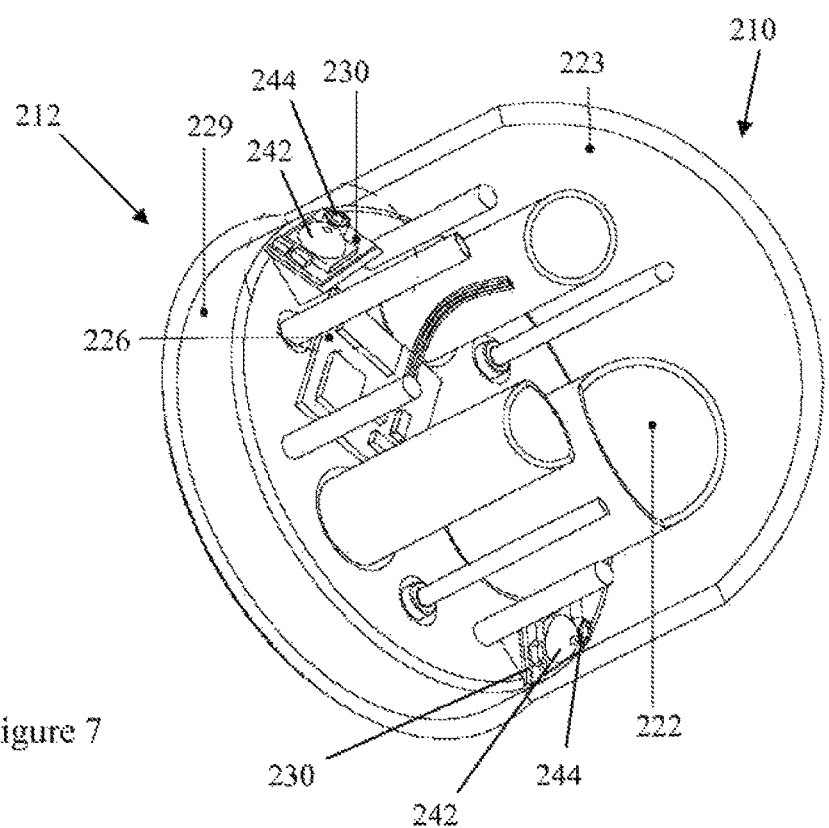
FIG. 7 shows a perspective view of an endoscope with rear-viewing imaging devices according to another embodiment of the present invention.
Figure 8:
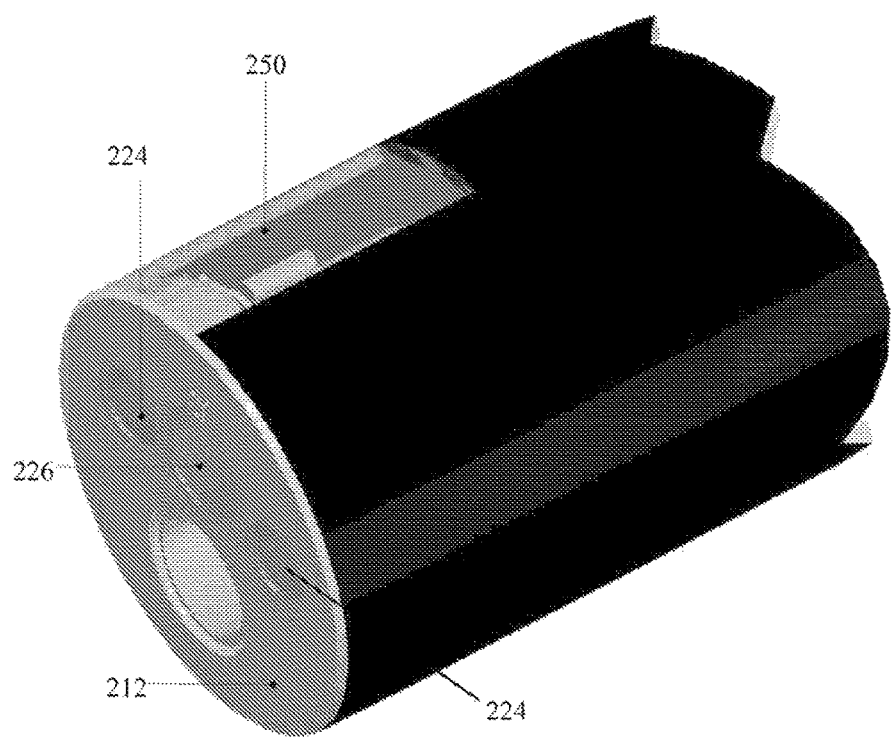
FIG. 8 shows a perspective view of the endoscope of FIG. 7 with windows for the rear-viewing imaging devices.

In accordance with another aspect of the invention, one or more rear-viewing imaging devices may be mounted in or on the distal end region of the insertion tube to provide retrograde views. FIGS. 7 and 8 illustrate an embodiment according to this aspect of the invention. In this embodiment, in addition to the main imaging device 226 and main light sources 224 (FIG. 8), the endoscope 210 also includes two rear-viewing imaging devices 230 mounted inside the distal end region of the insertion tube 212, although the endoscope 210 may include any number of rear-viewing imaging devices. Each rear-viewing imaging device 230 includes an imaging unit 242 and a light source 244. The sheath 223 of the insertion tube 212 may have a window 250 for each of the rear-viewing imaging devices 230 to "see" through. In this embodiment, each window 255 forms a portion of the cylindrical sheath 223 and may be dimensioned to maximize the field of view of the corresponding imaging device 230.

Figure 11:
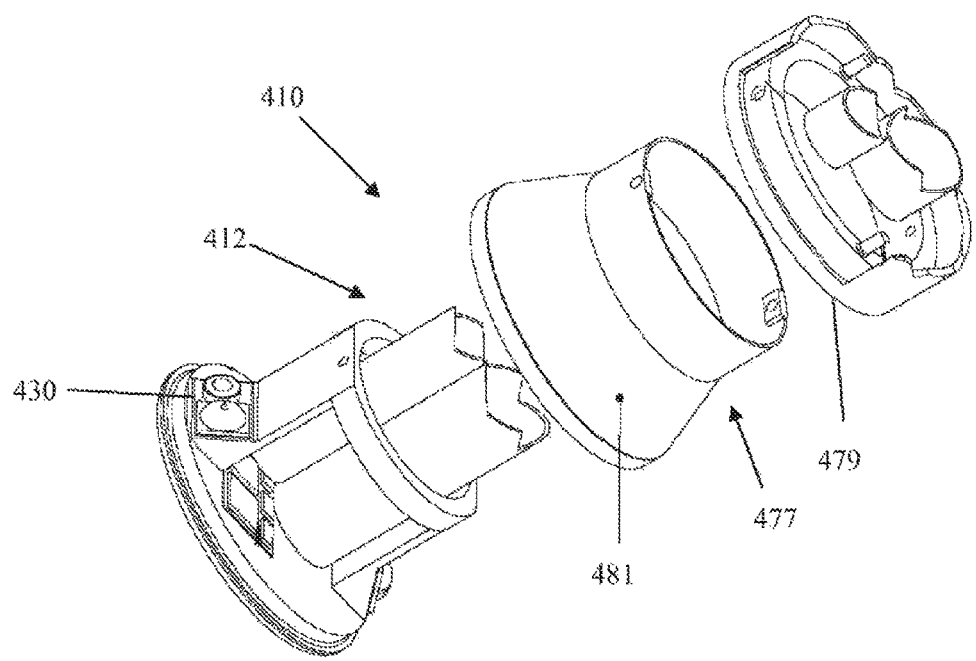
FIG. 11 shows a perspective view of a further endoscope with rear-viewing imaging devices.

In this embodiment, the imaging devices 230 are mounted on the proximal side of the insertion tube's end cap 229, although the rear-viewing imaging devices 230 may be mounted on any suitable structure of the insertion tube 212, such as shown in FIG. 11. Each of the rear-viewing imaging devices 230 is positioned to face a direction that is preferably within or equal to 90° from the longitudinal axis of the insertion tube 212, more preferably within or equal to 45° from the longitudinal axis of the insertion tube 212. Preferably, the direction that each rear-viewing imaging device 30 faces is optimized to provide the rear-viewing imaging device 30 with the largest field of view.

Figure 9:
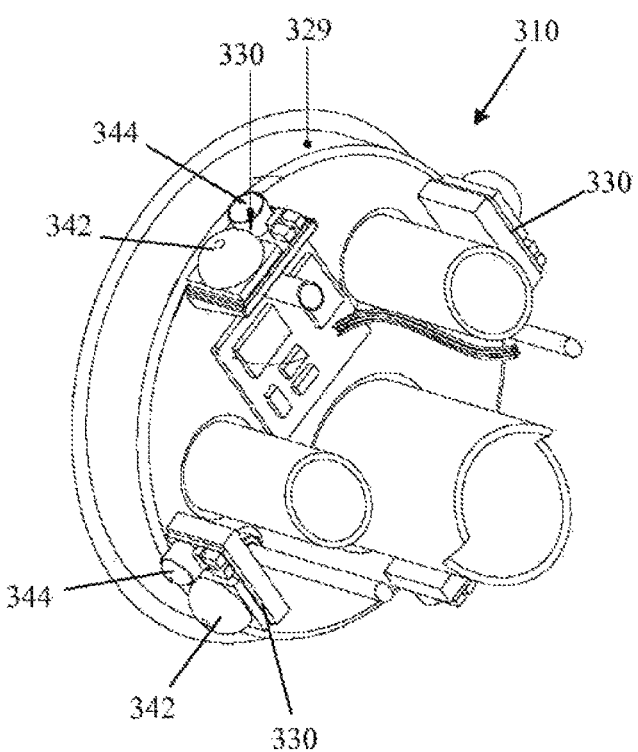
FIG. 9 shows a perspective view of another endoscope with rear-viewing imaging devices.
Figure 10:
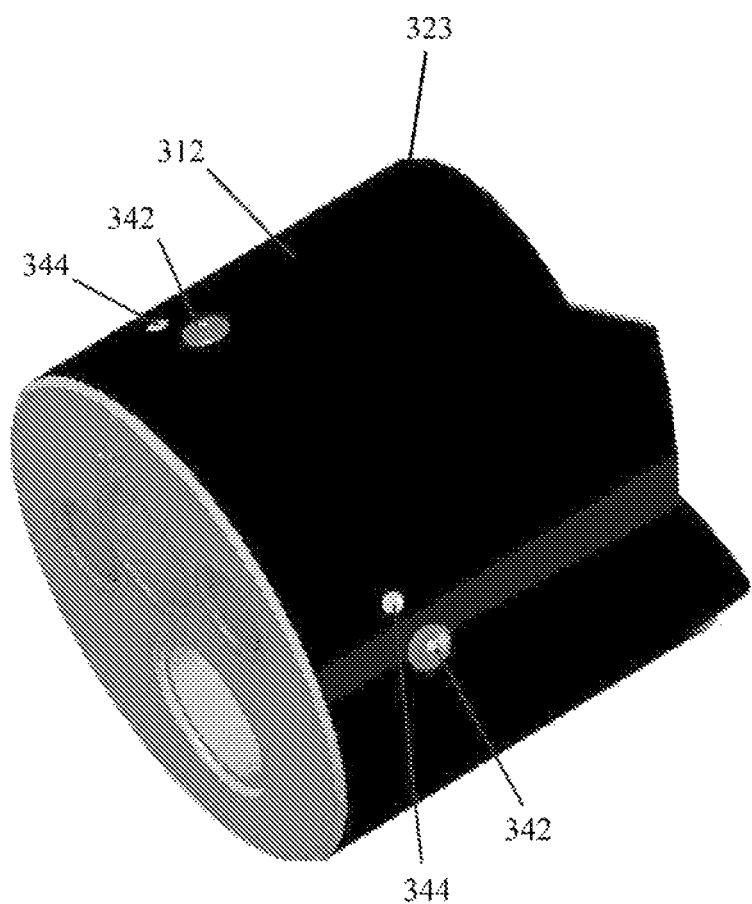
FIG. 10 shows a perspective view of the endoscope of FIG. 9 with the rear-viewing imaging devices protruding through the endoscope's sheath.

In addition to the embodiment shown in FIGS. 7 and 8, this aspect of the invention may have additional variations. For example, FIG. 9 illustrates an embodiment 310, in which the rear-viewing imaging devices 330 are mounted at a 90° angle from the longitudinal axis of the insertion tube 312. Each imaging device 330 includes an imaging unit 342 and a light source 344. Each rear-viewing imaging device 330 may be provided with a window, as shown in FIG. 8, or they may protrude from the sheath 323 as shown in FIG. 10. The rear-viewing imaging device 330 may be mounted on the proximal side of the insertion tube's end cap 329, as shown in FIG. 9, or on any suitable structure of the insertion tube 312, such as shown in FIG. 11.

Figure 12:
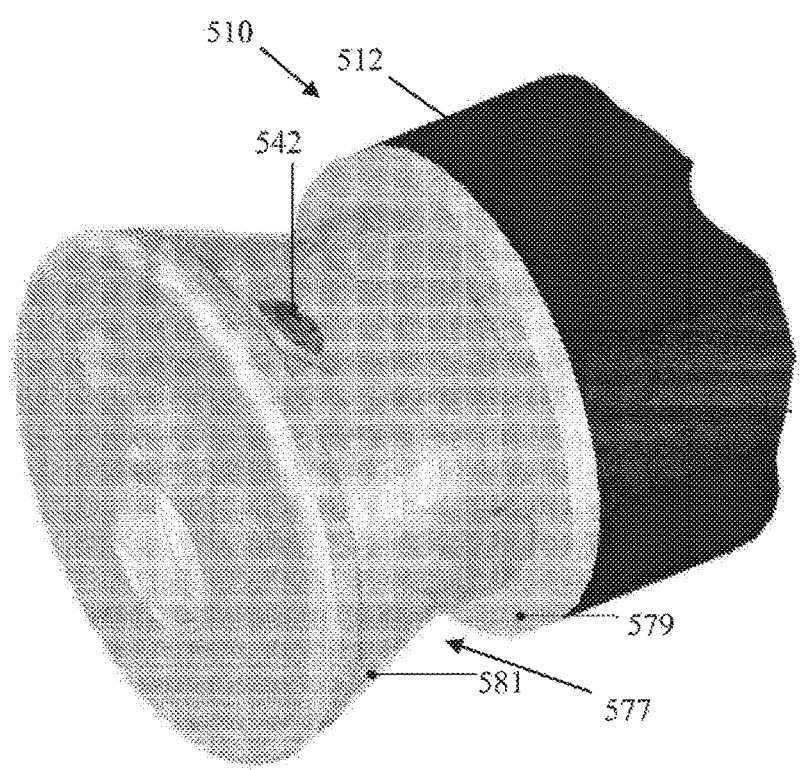
FIG. 12 shows a perspective view of the endoscope of FIG. 10 with the rear viewing imaging devices protruding through the rear-facing sidewall of a groove.

FIGS. 11 and 12 illustrate additional embodiments 410, 510 according to this aspect of the invention. In each of these embodiments 410, 510, an insertion tube 412, 512 has a circular groove 477, 577 with a front-facing sidewall 479, 579 and a rear-facing sidewall 481, 581. In the embodiment 410 shown in FIG. 11, the windows for the rear-viewing imaging devices 430 installed inside the insertion tube 412 are provided on the rear-facing sidewall 481 of the groove 477. In the embodiment 510 shown in FIG. 12, the imaging units 542 protrude from the rear-facing sidewall 581 of the groove 577.

Figure 13:
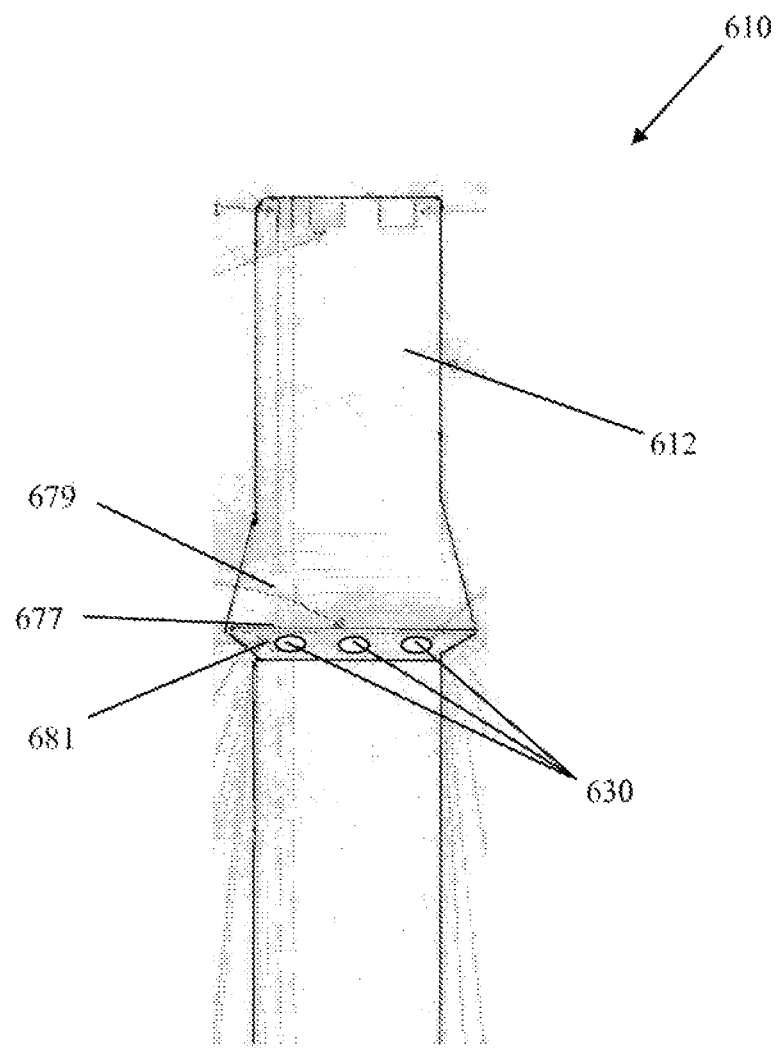
FIG. 13 shows a perspective view of a still further endoscope with the rear-viewing imaging devices provided on the rear-facing side of a circular protrusion.

FIG. 13 illustrates a further embodiment 610 according to this aspect of the invention. In this embodiment 610, the insertion tube 612 includes a circular protrusion 677 that has a front-facing side 679 and a rear-facing side 681. In this embodiment, imaging devices 630 are provided on the rear-facing side 681 of the circular protrusion 677. In general, however, imaging devices may also be provided on the distal end, front-facing side 679 of the circular protrusion 677.

The image data received from the rear-facing imaging devices may be combined to provide a 360° rear view. This may be accomplished by digitally combining or "stitching" the complementary images provided by individual rear-facing imaging devices into a single image. This may be done using hardware and/or software tools well known in the image processing industry. The rear-facing imaging devices may be positioned so as to capture an entire 360° rear view with a certain amount of overlap between the fields of view of adjacent imaging devices. An algorithm that is run on a computing device in the control box or connected to the control box may be used to compare the image data from adjacent imaging devices for matching image patterns, which indicate image overlaps. Then the overlaps are eliminated or reduced, and the images are combined to produce a single 360° rear image.

Figure 9A:
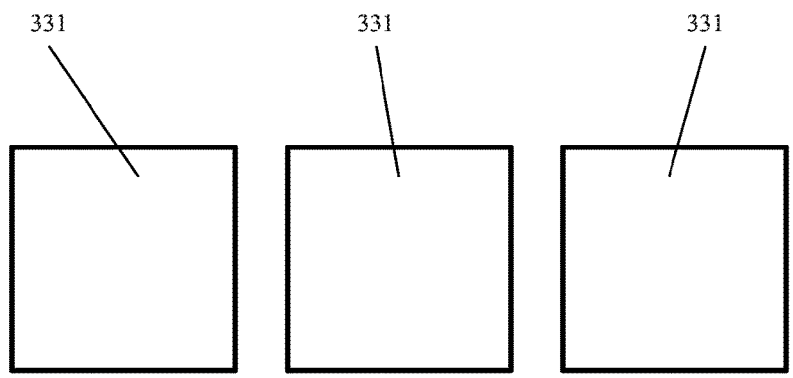
FIG. 9a schematically depicts display devices arranged to display images from the imaging devices of FIG. 9.

Alternatively, a number of display devices 331 corresponding to the number of rear viewing imaging devices 330 may be provided, as depicted in FIG. 9a. Each of the display devices may be used to display a distinct image from an imaging device. The display devices may be arranged in order, so as to simulate a continuous 360.degree. view.

Figure 14:
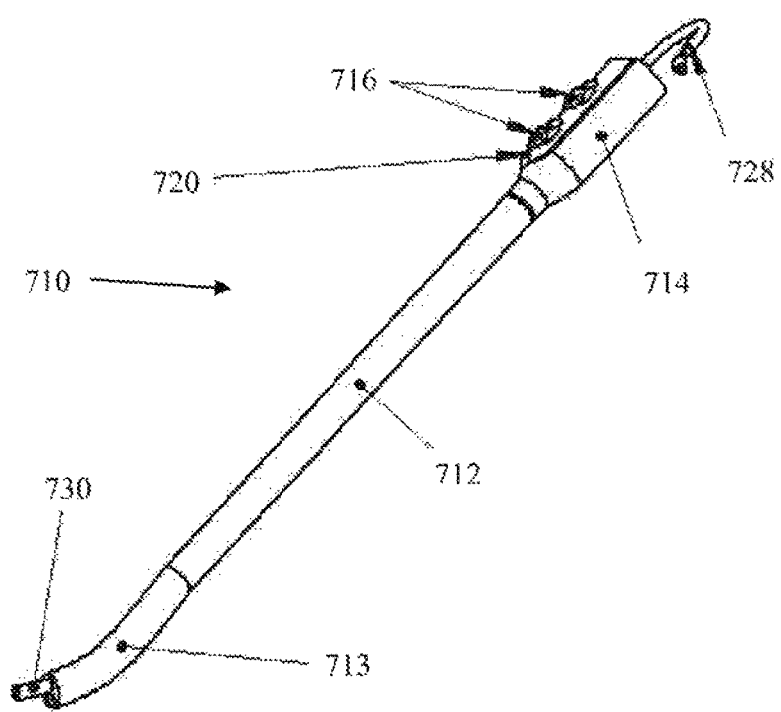
FIG. 14 shows a perspective view of an endoscope with a steerable imaging device according to a further embodiment of the present invention.

In accordance with a further aspect of the invention, an endoscope 710, as shown in FIG. 14, includes an insertion tube 712, a control handle 714 connected to the insertion tube 712, and an imaging device 730 extending from the distal end of the insertion tube 712.

Figure 15:
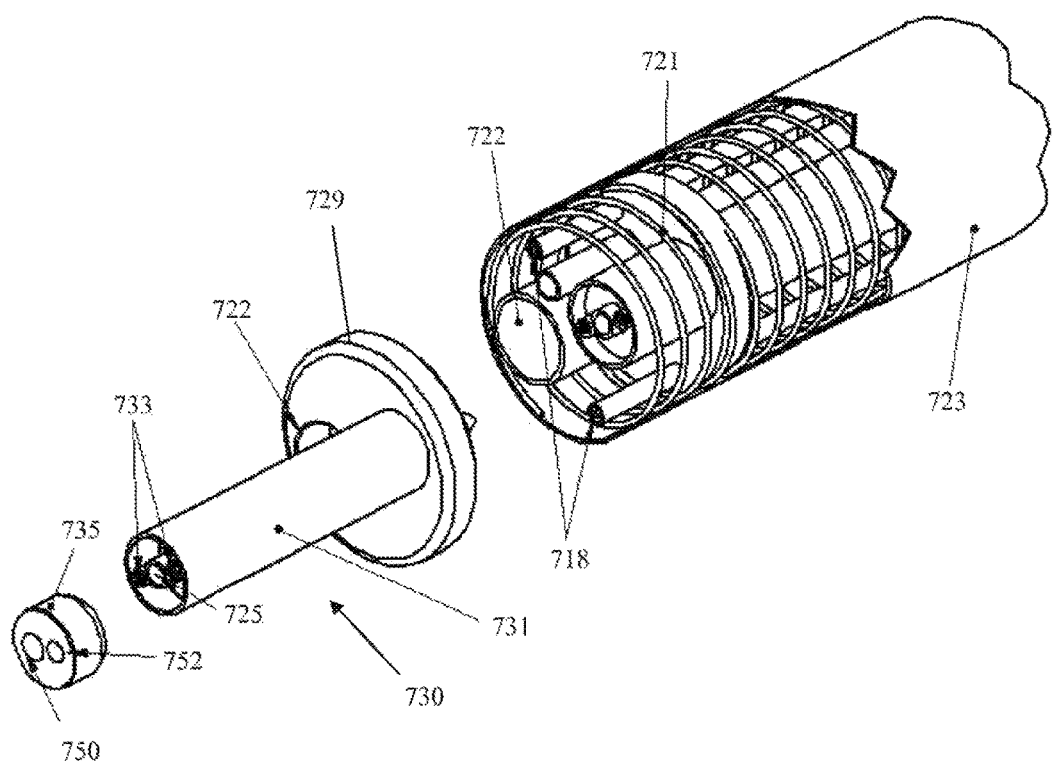
FIG. 15 shows a front perspective cutaway view of the endoscope of FIG. 14.

The insertion tube 712 of this embodiment, as shown in FIG. 15, may be similar to the insertion tube 12 shown in FIG. 1. For example, the insertion tube 712 may be detachable from the control handle 714 or may be integrally formed with the control handle 714. The insertion tube 712 preferably has a longitudinal channel 722 through which an instrument can reach the body cavity to perform any desired procedures. Preferably, the distal end region 713 of the insertion tube 712 is steerable (FIG. 14), and control cables 718 (FIG. 15) may be used to steer the distal end region 713. In this embodiment, the insertion tube 712 does not have a main imaging device at its distal end, although it may have such an imaging device in alternate embodiments. The insertion tube 712 may include a flexible ribbon coil 721 and a flexible sheath 723 that is used to protect the internal components of the insertion tube 712 from the environment of the body. An end cap 729 may be used to seal the open end of the shield 723 to close the distal end of the insertion tube 712.

As shown in FIG. 14, the control handle 714 may include one or more control knobs 716 that are attached to control cables 718 (FIG. 15) for the manipulation of the insertion tube 12. Preferably, the rotation of the control knobs 716 pulls the control cables 718 and therefore moves or bends the distal end region 713 of the insertion tube 712 up and down and/or side to side. Preferably, as shown in FIG. 14, the control handle 714 has one or more ports and/or valves 720. The ports and/or valves 720 are in communication with their respective channels 722 (FIG. 15) of the insertion tube 712. The ports and/or valves 720 can be air or water valves, suction valves, instrumentation ports, and suction/instrumentation ports. The proximal end of the control handle 714 may include an accessory outlet 728 that provides fluid communication between the air, water and suction channels and the pumps and related accessories. The same outlet or a different outlet can be used for electrical lines to light and imaging components at the distal end of the endoscope 10.

The imaging device 730 includes an extension 731 that extends from the distal end of the insertion tube 712, and one or more imaging units 750 and one or more light sources 752 that are mounted in the distal end region of the extension 731. In the illustrated embodiment, the extension 731 has a tubular configuration, and its diameter is approximately a third of the insertion tube's diameter. Similar to the insertion tube 712, the extension 731 may have a ribbon coil and a flexible sheath. The electrical wires for the imaging unit 750 and light source 752 may be routed through a channel 725 in the extension 731. Alternatively, the imaging unit 750 may be a wireless unit as described in U.S. patent application Ser. No. 11/609,838.

In this embodiment, at least the distal end region of the extension 731 is steerable to increase the areas accessible to the imaging unit 750. The extension 731 may be steered in a manner similar to how the insertion tube 712 is steered, i.e. by using Bowden cables 733. The first ends of the Bowden cables 733 may be attached to the proximal end of the extension's end cap 735, and the second ends may be attached to controls 716 on the handle 714 (FIG. 14). Accordingly, the handle 714 has two sets of controls 716 to articulate the distal end regions of the insertion tube 12 and extension 731.

Figure 16:
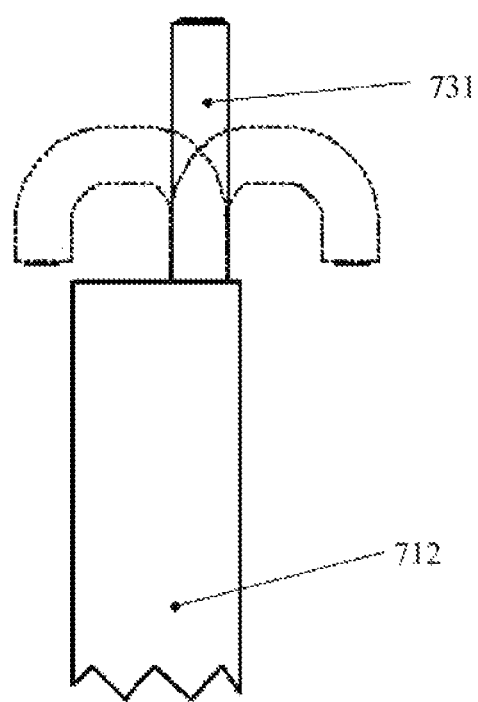
FIG. 16 shows an elevation view of the endoscope of FIG. 14 showing the steerability of the steerable imaging device.

The distal end region of the extension 731 may be steered up to 45°, 60°, 90°, 120°, 150°, or preferably 180° as shown in FIG. 16. The distal end region of the extension 731 may be steered in the direction of the channel 722 of the insertion tube 712 or in the direction of the axis of the insertion tube 712, and it may also be steered in the opposite direction. In other words, the distal end region of the extension 731 may be steered up to 180° in one direction and up to 180° in the opposite direction. In general, the distal end region may be steered in any number of directions, such as in only one direction or in three or more directions.

Figure 17:
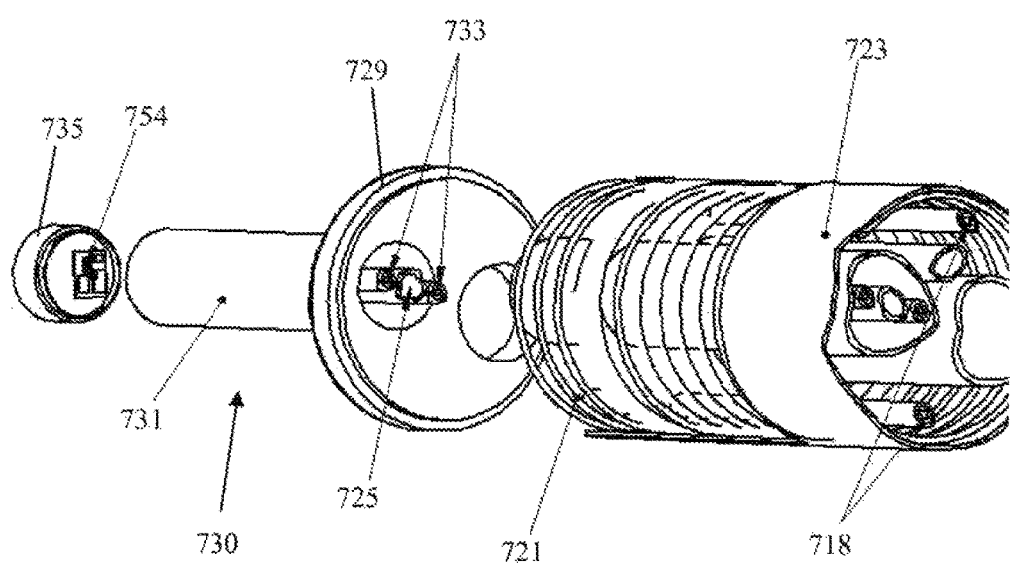
FIG. 17 shows a rear perspective cutaway view of the endoscope of FIG. 14.

The imaging unit 750 may have an image sensor (not shown) and a lens assembly (not shown) with associated circuitry which is integrated on a PCB 754. As shown in FIG. 17, this PCB 754 preferably is attached to the proximal side of the extension's end cap 735. Data output, control and power lines for the imaging unit 750 can be fed to the proximal end of the endoscope 710 to be interfaced via the handle 714 to the control box. Any additional processing of the signals may be done in the control box and finally fed to a display device.

The lens assembly comprising the lens or multiple lenses in a housing can be mounted directly onto the PCB 754 such that it overlies the image sensor and focuses the light entering the lens system onto the photosensitive area of the image sensor.

Figure 18:
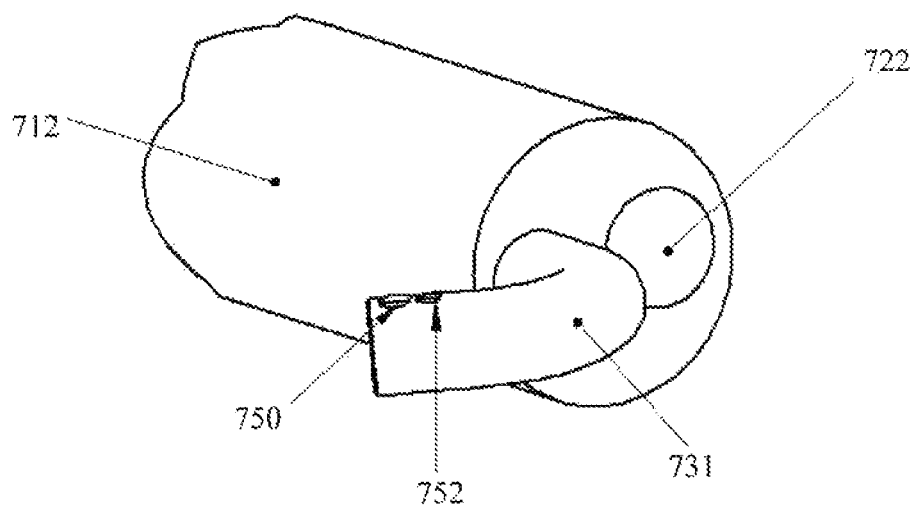
FIG. 18 shows a variation of the endoscope of FIG. 14 with a side-facing imaging unit.
Figure 19:
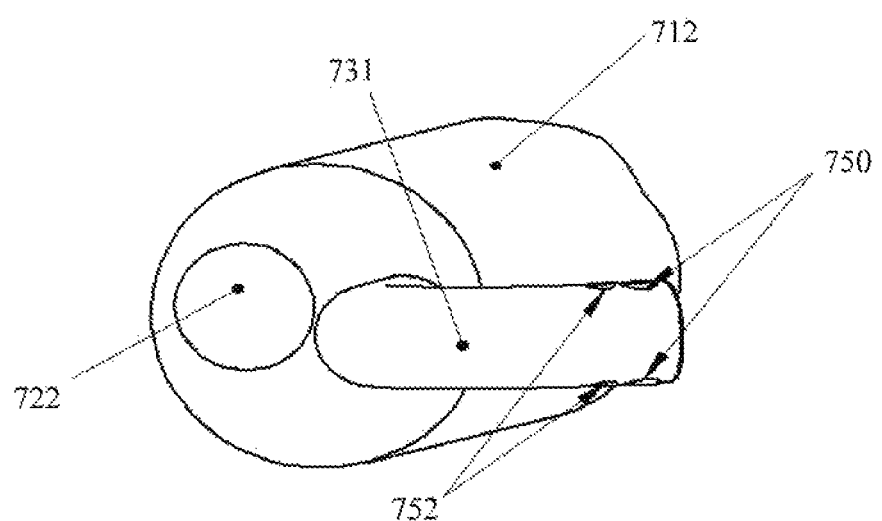
FIG. 19 shows another variation of the endoscope of FIG. 14 with two side-facing imaging units placed on the opposite sides of an extension.

The imaging units 750 and light sources 752 may be placed at any suitable location or locations in the distal end region of the extension 731. For example, as shown in FIG. 15, an imaging unit 750 and a light source 752 are placed on the distal end of the extension 731. Additionally or alternatively, as shown in FIG. 18, an imaging unit 750 and a light source 752 may be placed on a side of the distal end region of the extension 731. Furthermore, as shown in FIG. 19, imaging units 750 and light sources 752 may additionally or alternatively be placed on two opposite sides of the distal end region of the extension 731.

According to this aspect of the invention, both the extension 731 and the distal end region of the insertion tube 712 are steerable 180° in two directions. Consequently, the physician can better locate both the imaging unit 750 and the distal end of the insertion tube 712, resulting in a greater viewing field and allowing viewing of the areas behind folds and flexures. The steerable extension 731 is advantageous because it allows a greater degree of movement due to its smaller diameter and greater flexibility as compared to the distal end region of the insertion tube 712.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. An endoscope system comprising:
   an insertion tube comprising a sheath having a longitudinal axis, a longitudinal channel, and two windows that form a wall portion of the sheath and that are disposed on opposed lateral sides of the sheath, the insertion tube further comprising an end cap located at a distal-most end of the sheath;
   a first imaging device located at a distal end of the insertion tube;
   two side-mounted imaging devices, each mounted inside the sheath and on a proximal end surface of the end cap perpendicular to the longitudinal axis such that the two windows are disposed over each of the two side-mounted imaging devices; and
   a controller configured to combine image data from the two side-mounted imaging devices to simulate a continuous view; and
   wherein the first imaging device and each of the two side-mounted imaging devices each have an imaging unit and a light source, the first imaging device is mounted on a printed circuit board coupled to the proximal end surface of the end cap, and wherein the first imaging device and the two side-mounted imaging devices are configured to simultaneously acquire and output images.

2. The endoscope system of claim 1, wherein the simulated view is a 360 degree view.

3. The endoscope system of claim 1, wherein the controller is configured to compare image data from each of the side-mounted imaging devices to identify overlap regions and to eliminate the overlap regions to simulate the continuous view.

4. The endoscope system of claim 3, wherein the continuous view is a 360 degree view.

5. The endoscope system of claim 1, wherein the controller further comprises a first parameter-control register that corresponds to the first imaging device and two parameter-control registers that correspond to each of the two side-mounted imaging devices, wherein each parameter-control register is addressed by a unique number.

6. The endoscope system of claim 5, wherein the controller is configured to adjust parameters of the first imaging device and each of the two side-mounted imaging devices by writing data commands to the parameter-control registers.

7. The endoscope system of claim 6, wherein each of the two side-mounted imaging devices comprises a signal processing circuit configured to decode the data commands and to transmit the decoded commands to the imaging unit.

8. A tip section of a multi-camera endoscope, the tip section comprising:
   a sheath having a wall portion and an end cap located at a distal-most end of the sheath;

a front-pointing camera and a discrete front illuminator associated therewith, the front-pointing camera configured to output image data to a first display device and wherein the front-pointing camera and front illuminator are mounted on a printed circuit board coupled to a proximal end surface of the end cap:

two side-pointing cameras mounted inside the sheath and on the proximal end surface of the end cap perpendicular to a longitudinal axis of the sheath, wherein each of said two side-pointing cameras has a discrete side illuminator associated therewith, are each mounted to the proximal end surface of the end cap, and are disposed on opposed lateral sides of the sheath;

two windows that form a portion of the wall portion of the sheath, the two windows disposed over each of the two side-pointing cameras and the side illuminators;

a working channel configured for insertion of a surgical tool; and a controller configured to combine image data from the two side-pointing cameras to simulate a continuous view.

9. The tip section according to claim 8, further comprising a pathway fluid injector for inflating and/or cleaning a body cavity into which the endoscope is inserted.

10. The tip section according to claim 8, further comprising a fluid injector configured for cleaning said front-pointing camera and/or said discrete front illuminator.

11. The tip section according to claim 8, further comprising a third side-pointing camera positioned essentially at equal distances from each of the two side-pointing cameras along a circumference of the sheath.

12. The tip section according to claim 8, wherein said discrete front illuminator comprises a light-emitting diode (LED).

13. The tip section according to claim 8, wherein each of said discrete side illuminators comprises a light-emitting diode (LED).

14. The tip section according to claim 8, wherein each of said discrete front and side illuminators comprises a light-emitting diode (LED).

15. The tip section according to claim 8, wherein said endoscope is a colonoscope.

16. A multi-camera endoscope comprising:

an elongated shaft terminating with a tip section turnable by way of a bending section, wherein said tip section comprises:

a sheath having a wall portion and an end cap located at a distal-most end of the sheath;

a front-pointing camera and a discrete front illuminator associated therewith, and wherein the front-pointing camera and front illuminator are mounted on a printed circuit board coupled to a proximal end surface of the end cap;

two or more side-pointing cameras mounted inside the sheath and on the proximal end surface of the end cap perpendicular to a longitudinal axis of the sheath, wherein each of said two or more side-pointing cameras has a discrete side illuminator associated therewith and the two side-pointing cameras are each mounted to the proximal end surface of the end cap, and are disposed on opposed lateral sides of the tip section;

two windows that form a wall portion of the sheath, the two windows disposed over each of the two side-pointing cameras and the side illuminators; and a working channel configured for insertion of a surgical tool; and a controller configured to combine image data from the two side-pointing cameras to simulate a continuous view.

17. The endoscope according to claim 16, wherein said tip section further comprises a pathway fluid injector for inflating and/or cleaning a body cavity into which the endoscope is inserted.

18. The endoscope according to claim 16, wherein said tip section further comprises a fluid injector configured for cleaning said front-pointing camera and/or said discrete front illuminator.

19. The endoscope according to claim 16, wherein said discrete front illuminator comprises a light-emitting diode (LED).

20. The endoscope according to claim 16, wherein each of said discrete side illuminators comprises a light-emitting diode (LED).

21. The endoscope according to claim 16, wherein each of said discrete front and side illuminators comprises a light-emitting diode (LED).

22. The endoscope according to claim 16, wherein said endoscope is a colonoscope.

* * * * *